(12) United States Patent
Harding

(10) Patent No.: US 11,173,166 B2
(45) Date of Patent: Nov. 16, 2021

(54) COMPOSITION AND USES THEREOF

(71) Applicant: BH Biotech Pty Ltd, Morningside (AU)

(72) Inventor: Angus Harding, Morningside (AU)

(73) Assignee: BH Biotech Pty Ltd, Morningside (AU)

(*) Notice: Subject to any disclaimer, the term of this patent is extended or adjusted under 35 U.S.C. 154(b) by 23 days.

(21) Appl. No.: 16/647,270

(22) PCT Filed: Sep. 18, 2018

(86) PCT No.: PCT/AU2018/051021
§ 371 (c)(1),
(2) Date: Mar. 13, 2020

(87) PCT Pub. No.: WO2019/051565
PCT Pub. Date: Mar. 21, 2019

(65) Prior Publication Data
US 2020/0206246 A1 Jul. 2, 2020

(30) Foreign Application Priority Data

Sep. 18, 2017 (AU) ................................ 2017903793

(51) Int. Cl.
| | |
|---|---|
| *A61K 36/00* | (2006.01) |
| *A61K 31/58* | (2006.01) |
| *A61P 29/00* | (2006.01) |
| *A61K 9/00* | (2006.01) |
| *A61K 31/121* | (2006.01) |
| *A61K 31/202* | (2006.01) |
| *A61K 31/4525* | (2006.01) |
| *A61K 36/67* | (2006.01) |
| *A61K 36/81* | (2006.01) |
| *A61K 36/9066* | (2006.01) |

(52) U.S. Cl.
CPC ............ *A61K 31/58* (2013.01); *A61K 9/0053* (2013.01); *A61K 31/121* (2013.01); *A61K 31/202* (2013.01); *A61K 31/4525* (2013.01); *A61K 36/67* (2013.01); *A61K 36/81* (2013.01); *A61K 36/9066* (2013.01); *A61P 29/00* (2018.01)

(58) Field of Classification Search
None
See application file for complete search history.

(56) References Cited

U.S. PATENT DOCUMENTS

| | | |
|---|---|---|
| 2011/0064712 A1 | 3/2011 | Amato |
| 2013/0338039 A1 | 12/2013 | Mazed et al. |
| 2014/0271944 A1 | 9/2014 | Mccord et al. |
| 2014/0287071 A1* | 9/2014 | Barnett, III ............ A61K 36/82 424/729 |

FOREIGN PATENT DOCUMENTS

| | | |
|---|---|---|
| KR | 20110002163 | 1/2011 |
| WO | 2007/003762 | 1/2007 |
| WO | 2016/101028 | 6/2016 |

OTHER PUBLICATIONS

Borre et al. "Neuroprotective and cognitive enhancing effects of a multi-targeted food intervention in an animal model of neurodegeneration and depression", Neuropharmacology 79:738-749 (2014).
Calder et al. "Polyunsaturated fatty acids, inflammation and immunity", European Journal of Clinical Nutrition 56(3): S14-S19 (2002).
Fritsche "The Science of Fatty Acids and Inflammation", Adv Nutr 6:293S-301S (2015).
International Search Report and Written Opinion corresponding to International Application No. PCT/AU2018/051021 dated Dec. 17, 2018.
International Preliminary Report on Patentability corresponding to International Application No. PCT/AU2018/051021 dated 2018.
Kong et al. "Curcumin Represses NLRP3 Inflammasome Activation via TLR4/MyD88/NF-kB and P2X7R Signaling in PMA-Induced Macrophages", Frontiers in Pharmacology 7:Article 369 pp. 1-10 (2016).
Pandit et al. "Evaluation of herb-drug interaction of a polyherbal Ayurvedic formulation through high throughput cytochrome P450 enzyme inhibition assay", Journal of Ethnopharmacology 197:165-172 (2017).

* cited by examiner

*Primary Examiner* — Qiuwen Mi
(74) *Attorney, Agent, or Firm* — Myers Bigel, P.A.

(57) ABSTRACT

The present invention relates to compositions for inhibiting inflammation. The composition can comprise one or more natural products in the form of a nutraceutical or functional food. The present invention further relates to the combinatorial use of nutritional supplements and nutraceuticals for the prevention and/or treatment of sterile inflammation and conditions associated with sterile inflammation.

12 Claims, 18 Drawing Sheets

A

B

C

A

B

| Treatment | Mean Relative Inhibition |
|---|---|
| Control | 0.01351 |
| Ashwaganda | 0.1938 |
| Turmeric | 0.1734 |
| Ashwaganda + Turmeric | 0.509 |

C

A

B

| Treatment | Mean Relative Inhibition |
|---|---|
| Control | 0 |
| Turmeric | 0.2942 |
| Pepper | 0.2511 |
| Turmeric + Pepper | 0.6103 |

A

B

| Treatment | Mean Relative Inhibition |
|---|---|
| Control | 0.01643 |
| Ashwaganda | 0.1505 |
| Pepper | 0.1937 |
| Ashwaganda + Pepper | 0.3524 |

A

B

A

B

| Treatment | Mean Relative Inhibition |
|---|---|
| Control | 0 |
| Ashwaganda | 0.1533 |
| DHA | 0.3256 |
| Ashwaganda + DHA | 0.5657 |

A

B

| Treatment | Mean Relative Inhibition |
|---|---|
| Control | 0 |
| Turmeric | 0.184 |
| DHA | 0.2554 |
| Turmeric + DHA | 0.546 |

COMPOSITION AND USES THEREOF

STATEMENT OF PRIORITY

This application is a 35 U.S.C. § 371 national phase application of PCT Application No. PCT/AU2018/051021 filed Sep. 18, 2018, which claims priority to Australian Application No. 2017903793 filed Sep. 18, 2017, the entire contents of each of which is incorporated by reference herein.

TECHNICAL FIELD

The present invention relates to compositions for inhibiting inflammation. The composition can comprise one or more natural products in the form of a nutraceutical or functional food. The present invention further relates to the combinatorial use of nutritional supplements and nutraceuticals for the prevention and/or treatment of sterile inflammation and conditions associated with sterile inflammation.

BACKGROUND ART

Sterile Inflammation

Inflammation is mediated by the innate immune system and is an essential function that occurs in response to pathogens during infection, and within a sterile context in response to a traumatic or chemically induced injury, a process known as sterile inflammation (Chen and Nunez, 2010; Guo et al., 2015). In both cases, signals at the site of infection or injury recruit innate immune cells, primarily macrophages and neutrophils, by binding to and activating pattern-recognition receptors (PRRs) (Chen and Nunez, 2010; Guo et al., 2015). Activation of PRRs by pathogen associated molecular patterns (PAMPs) in the context of infection, and damage associated molecular patterns (DAMPs) in the context of sterile inflammation triggers the assembly of multimeric protein complexes within the cytosol of macrophages and other innate immune cells, collectively named inflammasomes (Guo et al., 2015). Although there exist a number of different inflammasome complexes, which respond to different stimuli and utilise different proteins for their assembly, the general function of inflammasomes is to act as a caspase-1 activating scaffold (Guo et al., 2015). Caspase-1 activation catalyses the maturation and subsequent secretion of the pro-inflammatory cytokines IL-1β and IL-18 (Guo et al., 2015).

Sterile inflammation plays an essential role in the healing process. Physical trauma, ischaemia-reperfusion injuries or chemically induced injuries activate signalling cascades that recruit cells of the innate immune system, most importantly macrophages, to the site of trauma to trigger an inflammatory response (Leemans et al., 2011). Sterile inflammation that is appropriately initiated at the site of injury drives tissue remodelling and wound healing (Leemans et al., 2011). Once the wound has healed, the inflammatory stimuli are removed, and inflammation resolves.

Although inflammation is beneficial in many contexts, poorly regulated or low-level, chronic inflammation has been shown to potentiate multiple disease states such as cancer, neurodegenerative diseases, and autoimmunity. Failure to resolve the inflammatory signal generates a chronic sterile inflammatory response, which if left untreated contributes towards many serious health conditions in humans (Kapetanovic et al., 2015; Nakahira et al., 2015), as set out in Table 1. In these contexts, there is great need for therapeutic drugs that can inhibit inflammation without resulting in severe or complicating side effects (Mangan et al., 2018).

TABLE 1

Conditions where chronic NLRP3 activation has been shown to contribute to disease progression
Health Conditions linked to chronic NLRP3 Inflammasome Activation Aging (Ferrucci and Fabbri, 2018; Goldberg and Dixit, 2015; Kapetanovic et al., 2015)
Allergy (Xiao et al., 2018)
Alzheimers (Heneka et al., 2013; Pennisi et al., 2017)
Atherosclerosis (Koelwyn et al., 2018; Tabas and Bornfeldt, 2016)
Arthritis (Marchetti et al., 2018; Mathews et al., 2014; Snouwaert et al., 2016; Vande Walle et al., 2014)
Auto-inflammatory disease (Mortimer et al., 2016; Zhong et al., 2016)
Cancer (Chow et al., 2012; Goldberg and Dixit, 2015; Guo et al., 2014)
Colitis (Guo et al., 2014; Zhang et al., 2014)
Diabetes (Esser et al., 2014; Ferrucci and Fabbri, 2018; Pavillard et al., 2018)
Gout and pseudogout (Nakayama, 2018; So and Martinon, 2017)
Ischemia-perfusion (Guo et al., 2016; Minutoli et al., 2016)
Macular Degeneration (Gao et al., 2015; Goldberg and Dixit, 2015; Marneros, 2013)
Neurodegeneration (Debye et al., 2018; Lee et al., 2018; Rubartelli, 2014)
Obesity (Haneklaus and O'Neill, 2015; Pavillard et al., 2018)
Osteoarthritis (Conway and McCarthy, 2018; Ferrucci and Fabbri, 2018; McAllister et al., 2018)
Osteoporosis, Sarcopenia and Frailty (Conway and McCarthy, 2018; Ferrucci and Fabbri, 2018; McBride et al., 2017; Snouwaert et al., 2016; Wang et al., 2017; Xu et al., 2018)
Stress and Mood Disorders (Fleshner et al., 2017; Herman and Pasinetti, 2018; Kaufmann et al., 2017)

Immune Response

The most important cell type for triggering sterile inflammation is the monocyte/macrophage. In the blood, circulating monocytes enter different tissues of the body to differentiate into mature macrophages (Peiseler and Kubes, 2018). Macrophages are phenotypically plastic and undergo dynamic phenotypic switching in response to micro-environmental signals (Dunster, 2016).

During the initial stages of infection or injury, macrophages adopt a pro-inflammatory phenotype that produce pro-inflammatory cytokines IL1β and IL-18, and increase the expression pattern recognition receptors and inflammasomes such as NLRP3 (Peiseler and Kubes, 2018). Macrophages also contribute to chronic inflammation that is the hallmark of auto-inflammatory disease (Peiseler and Kubes, 2018). For example, macrophages contribute to the formation of inflammatory plaques in the walls of blood vessels in atherosclerosis (Geeraerts et al., 2017), and macrophage recruitment to the site of injury or inflammation within the central nervous system represents one of the initial signature events during neuro-inflammation, and is a hallmark of pathogenesis associated with various neurodegenerative diseases (Sevenich, 2018).

The NLRP3 Inflammasome

The NLRP3 inflammasome is expressed in many cell types in multiple human tissues (including monocytes, macrophages, neutrophils, dendritic cells, microglia, astrocytes, neurons and endothelial cells (Guarda et al., 2011; Zhou et al., 2016)), and is activated by a wide range of pro-inflammatory stimuli, which explains why the NLRP3 inflammasome contributes to so many health conditions (as summarised in Table 1). Inflammatory stimuli known to activate the NLRP3 inflammasome in the absence of pathogens include reactive oxygen species (ROS), ATP, crystalline substances and DNA (Mangan et al., 2018). NLRP3 activation typically occurs during a two-step process, starting with an initial priming phase that is followed by inflammasome activation (Mangan et al., 2018). The priming signal involves activation of the NF-κβ pathway by Toll-Like Receptor (TLR) agonists, reactive oxygen species and pro-inflammatory cytokines leading to the increased expression and stability of the NLRP3 protein (Mangan et al., 2018). A second distinct signal such as NLRP3 recruitment to the mitochondria, release of mitochondrial reactive-oxygen species and mitochondrial DNA, potassium efflux and cathepsin release from damaged lysosomes (Chen and Nunez, 2010) trigger NLRP3 oligomerization and caspase-1 activation (Mangan et al., 2018).

IL-β—Background and Downstream Effects

One of the primary pro-inflammatory cytokines produced by macrophages during inflammation is IL-1β. While IL-1β is made in a variety of contexts, activation of the NLRP3 inflammasome is a well-studied mediator of this response that occurs in many human diseases.

Specifically, IL-1β is translated in macrophages during NLRP3 activation as an inactive pro-protein that is cleaved by caspase-1 and secreted as the pro-inflammatory cytokine (Lopez-Castejon and Brough, 2011). The inflammatory cytokine IL-1β is a master regulator of inflammation and controls diverse inflammatory phenotypes at the cellular level including the recruitment activation of immune cells, the release of inflammatory signals such as nitric oxide and chemokines, as well as mediating gross metabolic and physiologic changes associated with inflammation such as fever and cortisol release. IL-1β is also linked with diseases associated with chronic sterile inflammation (Dinarello, 2011).

Due to the prevalence of diseases and health condition involving chronic sterile inflammation, there is great need for therapeutic drugs that can inhibit inflammation without resulting in severe or complicating side effects. There is a particular need for new therapeutics that can be used to safely treat a disease state involving sterile inflammation for long periods of time.

It will be clearly understood that, if a prior art publication is referred to herein, this reference does not constitute an admission that the publication forms part of the common general knowledge in the art in Australia or in any other country.

SUMMARY OF INVENTION

The present invention is directed to a composition for inhibiting inflammation, which may at least partially overcome at least one of the abovementioned disadvantages or provide the consumer with a useful or commercial choice.

With the foregoing in view, the present invention in one form, resides broadly in a composition comprising one or more natural products. Preferably, the composition comprises one or more natural products in a synergistic combination.

Preferably, the natural products are selected from compounds that can be isolated from cruciferous vegetables, compounds that can be isolated from plants of the genera *Withania, Brassica, Armoracia, Barbarea, Diplotaxis, Eruca, Lepidium, Nasturtium, Raphanus, Wasabia, Curcuma, Piper, Gardenia, Berberis, Silybum, Plectranthus, Vitis, Vaccinum, Rubus, Rheum,* or *Cannabis,* and compounds that can be isolated from various plants, including but not limited to rhubarb, buckthorn, Japanese knotweed, black pepper, and wheat germ.

In particularly preferred embodiments, the composition can comprise one or more natural products selected from the group consisting of withaferin A, sulforaphane, berteroin, genipin, berberine, resveratrol, emodin, piperine, spermidine, beta-hydroxybutyric acid, silybin, forskolin, indole-3-carbinol and cannabidiol.

Even more preferably, the composition comprises two or more compounds or extracts selected from withaferin A (derived from *Withania somnifera*), curcumin (derived from *Curcuma longa*), and piperine (derived from *Piper nigrum*).

In another aspect, the invention resides broadly in a method of protecting a subject from sterile inflammation, the method comprising administering to the subject a therapeutically effective amount of a composition comprising one or more natural products selected from the group consisting of withaferin A, sulforaphane, berteroin, genipin, berberine, resveratrol, emodin, piperine, spermidine, beta-hydroxybutyric acid, silybin, forskolin, indole-3-carbinol and cannabidiol.

Optionally, the method can further comprise dietary intervention, such as the inclusion of omega-3 fatty acids in the diet, or the addition of omega-3 fatty acids as a supplement.

Preferably, the method comprises administering to the subject a therapeutically effective amount of a composition comprising two or more compounds or extracts selected from withaferin A (derived from *Withania somnifera*), curcumin (derived from *Curcuma longa*), and piperine (derived from *Piper nigrum*).

Optionally, the method can further comprise dietary intervention, such as the inclusion of omega-3 fatty acids in the diet, or the addition of omega-3 fatty acids as a supplement.

In another aspect, the invention resides broadly in a method of treating and/or preventing a condition associated with sterile inflammation, the method comprising administering to the subject a therapeutically effective amount of a composition comprising one or more natural products selected from the group consisting of withaferin A, sulforaphane, berteroin, genipin, berberine, resveratrol, emodin, piperine, spermidine, beta-hydroxybutyric acid, silybin, forskolin, indole-3-carbinol and cannabidiol.

Optionally, the method can further comprise dietary intervention, such as the inclusion of omega-3 fatty acids in the diet, or the addition of omega-3 fatty acids as a supplement.

Preferably, the method comprises administering to the subject a therapeutically effective amount of a composition comprising two or more compounds or extracts selected from withaferin A (derived from *Withania somnifera*), curcumin (derived from *Curcuma longa*), and piperine (derived from *Piper nigrum*).

Optionally, the method can further comprise dietary intervention, such as the inclusion of omega-3 fatty acids in the diet, or the addition of omega-3 fatty acids as a supplement.

In another aspect, the invention resides broadly in the use of one or more natural products selected from the group consisting of withaferin A, sulforaphane, berteroin, genipin, berberine, resveratrol, emodin, piperine, spermidine, beta-hydroxybutyric acid, silybin, forskolin, indole-3-carbinol and cannabidiol, in the manufacture of a medicament for protecting a subject from sterile inflammation.

In another aspect, the invention resides broadly in the use of two or more compounds or extracts selected from witha-ferin A (derived from *Withania somnifera*), curcumin (derived from *Curcuma longa*), and piperine (derived from

*Piper nigrum*), in the manufacture of a medicament for protecting a subject from sterile inflammation.

In another aspect, the invention resides broadly in the use of one or more natural products selected from the group consisting of withaferin A, sulforaphane, berteroin, genipin, berberine, resveratrol, emodin, piperine, spermidine, beta-hydroxybutyric acid, silybin, forskolin, indole-3-carbinol and cannabidiol, in the manufacture of a medicament for treating and/or preventing a condition associated with sterile inflammation.

In another aspect, the invention resides broadly in the use of two or more compounds or extracts selected from withaferin A (derived from *Withania somnifera*), curcumin (derived from *Curcuma longa*), and piperine (derived from *Piper nigrum*), in the manufacture of a medicament for treating and/or preventing a condition associated with sterile inflammation.

In another aspect, the invention resides broadly in the use of one or more natural products selected from the group consisting of withaferin A, sulforaphane, berteroin, genipin, berberine, resveratrol, emodin, piperine, spermidine, beta-hydroxybutyric acid, silybin, forskolin, indole-3-carbinol and cannabidiol, for protecting a subject from sterile inflammation.

Additionally, dietary intervention, such as the inclusion of omega-3 fatty acids in the diet or provided as a supplement can be used to provide improved protection from sterile inflammation.

In another aspect, the invention resides broadly in the use of two or more compounds or extracts selected from withaferin A (derived from *Withania somnifera*), curcumin (derived from *Curcuma longa*), and piperine (derived from *Piper nigrum*), for protecting a subject from sterile inflammation.

Optionally, dietary intervention, such as the inclusion of omega-3 fatty acids in the diet, alone or in combination with compounds or extracts selected from withaferin A (derived from *Withania somnifera*), curcumin (derived from *Curcuma longa*), and piperine (derived from *Piper nigrum*) can be used to provide improved protection from sterile inflammation.

In another aspect, the invention resides broadly in the use of one or more natural products selected from the group consisting of withaferin A, sulforaphane, berteroin, genipin, berberine, resveratrol, emodin, piperine, spermidine, beta-hydroxybutyric acid, silybin, forskolin, indole-3-carbinol and cannabidiol, for treating and/or preventing a condition associated with sterile inflammation.

Additionally, dietary intervention, such as the inclusion of omega-3 fatty acids in the diet, can also be used to provide improved outcomes in treating and/or preventing a condition associated with sterile inflammation.

In another aspect, the invention resides broadly in the use of two or more compounds or extracts selected from withaferin A (derived from *Withania somnifera*), curcumin (derived from *Curcuma longa*), and piperine (derived from *Piper nigrum*), for treating and/or preventing a condition associated with sterile inflammation.

Optionally, dietary intervention, such as the inclusion of omega-3 fatty acids in the diet, can also be used with the two or more compounds or extracts to provide improved outcomes for treating and/or preventing a condition associated with sterile inflammation.

Compositions of the invention can further comprise pharmaceutically acceptable carriers, diluents and/or excipients. Pharmaceutically acceptable carriers, diluents and excipients which can be used in the compositions of the invention will be known to those of skill in the art. The British Pharmacopoeia (BP) and the United States Pharmacopeia and National Formulary (USP-NF) contain details of suitable carriers, diluents and excipients, as does Sweetman S (Ed.), 'Martindale: The complete drug reference.' London: Pharmaceutical Press, $37^{th}$ Ed., (2011), and Rowe R C, Sheskey P J, Quinn M E (Ed.), 'Handbook of Pharmaceutical Excipients', $6^{th}$ Ed., London: Pharmaceutical Press (2009), the contents of which are incorporated herein by cross reference.

The compositions of the invention can be formulated for oral administration. The compositions can thus be in the form of a powder, a liquid solution, a suspension, a dispersion, an emulsion, a tablet, a pill or a capsule.

In a particular embodiment, the compositions of the invention are formulated as a lipid complex. The lipid complex can comprise a single lipid, or a combination of two or more lipids.

In an alternative embodiment, compositions of the invention can be formulated into a nanoparticle delivery system.

In a further alternative embodiment, compositions of the invention can be formulated into a cyclodextrin-based carrier. This embodiment is advantageous, due to the characteristics of cyclodextrins. Specifically, as cyclodextrins are hydrophobic on their interior, and hydrophilic on their exterior, they can form complexes with hydrophobic compounds and extracts, and therefore act to enhance the solubility and thus bioavailability of natural compounds and plant extracts. Cyclodextrins can also enhance permeability of compounds and extracts through mucosal tissues. One or more of alpha-, beta- and gamma-cyclodextrins can be used as carriers in delivery systems in the present invention.

In a further alternative embodiment, compositions of the invention can be incorporated into a liposome structure consisting of a spherical vesicle having at least one lipid bilayer. The liposome can be used as a vehicle for administration of compositions of the invention. The liposomes can comprise phospholipids, in particular phosphatidylcholine, but can comprise other lipids that are compatible with formation of lipid bilayer structures and are useful for drug delivery.

Any of the features described herein can be combined in any combination with any one or more of the other features described herein within the scope of the invention.

The reference to any prior art in this specification is not, and should not be taken as an acknowledgement or any form of suggestion that the prior art forms part of the common general knowledge.

BRIEF DESCRIPTION OF DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows:

FIG. 1A is a standard curve generated using the BioLegend human IL-1β ELISA kit. FIG. 1B is a graph of the results of the THP-1 inflammasome assay.

DESCRIPTION OF EMBODIMENTS

Abbreviations and Definitions

Figure 1:
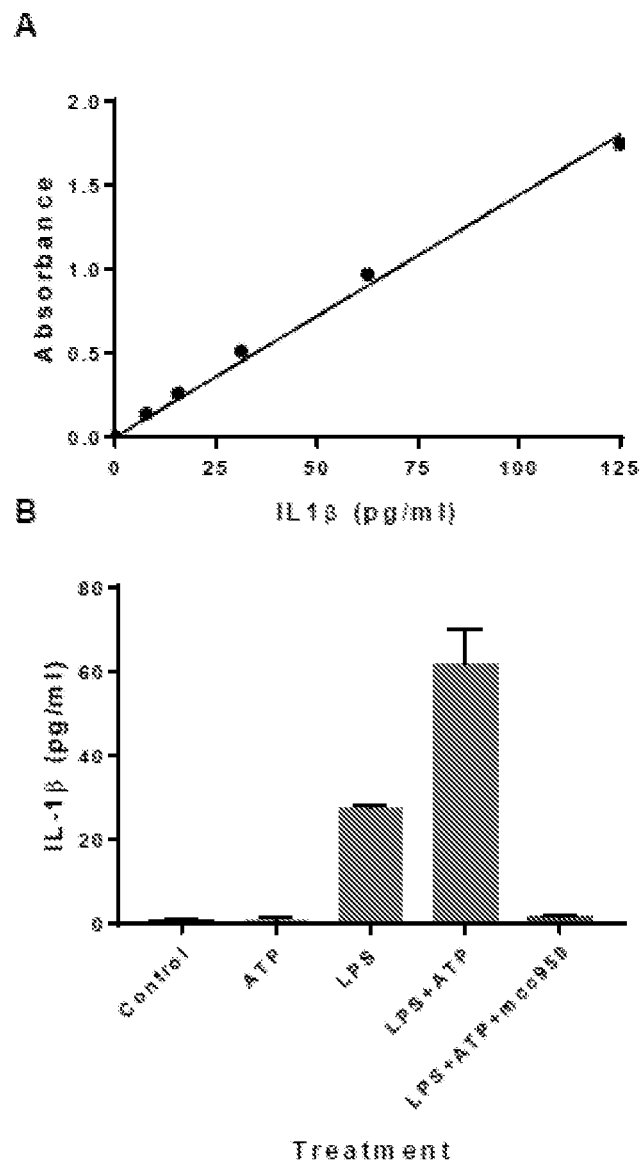
FIG. 1 illustrates validation of the use of the THP-1 cell line to study inflammation.

The following abbreviations and definitions are used throughout.

CI (combination index)=a quantitative measure of the degree of drug interaction in terms of synergism and antagonism synergism (CI<1)=greater than expected additive effect additive effect (CI=1)=the combined effect predicted in the absence of synergism and antagonism antagonism (CI>1)=smaller than expected additive effect Fa=fraction affected potentiation=a condition in which one of two drugs is not effective by itself, but increases the effect of the other drug m value=the shape parameter for the dose-response curve generated in Compusyn. The m value is the slope of the median effect plot. m=1, m<1 and m>1 indicate hyperbolic, sigmoidal and flat sigmoidal respectively.

r value=the conformity parameter for goodness of fit generated in Compusyn. For cell culture experiments the acceptable value is r≥0.9.

CBD=cannabidiol
DAMPS=damage associated molecular patterns
DHA=docosahexaenoic acid
DIM=3,3'-Diindolylmethane
ELISA=enzyme-linked immunosorbent assay
EPA=eicosapentaenoic acid
I3C=Indole-3 carbinol
IL-1β=interleukin-1 beta
IL-18=interleukin-18
LPS=lipopolysaccharide
NLRP3=NACHT, LRR and PYD domains-containing protein 3
PRRs=pattern-recognition receptors
ROS=reactive oxygen species
SFN=sulforaphane
THP-1=a human acute monocytic leukemia cell line
TLR=toll-like receptor

EXAMPLES

Materials and Methods

Compounds and Plant Extracts

Pure compounds were purchased from Cayman Chemicals. Pure omega-3 fatty acids, DHA and EPA, were purchased from Sigma Aldrich. Dried and powdered plant extracts from ashwagandha (*Withania somnifera*), turmeric (*Curcuma longa*), and pepper (*Piper nigrum*) dried powder preparations were purchased from Australian wholesale herbal manufacturers. Plant extracts were prepared from the powdered herb preparations using previously described methods (Delazar et al., 2012).

Cell Culture System

The human cell line THP-1 is the most frequently used cell line to study macrophage biology (Chanput et al., 2014). THP-1 cells provide many advantages for screening purposes including: 1) a rapid doubling time; 2) safety (there is no reported evidence of infectious virus or toxic products in THP-1 cells); 3) immortalized THP-1 cells can be passaged up to 25 times without a significant change in phenotype or biological activity; 4) THP-1 cells can be stored indefinitely in liquid nitrogen; and 4) THP-1 cells have a homogenous genetic background, meaning that consistent and reproducible data can be generated across assays for robust statistical analyses (Chanput et al., 2014).

Human monocytic THP-1 cells were purchased from CellBank Australia and maintained in RPMI 1640 culture medium containing 10% heat inactivated fetal bovine serum and supplemented with 10 mM Hepes, 1 mM pyruvate, 2.5 g/L D-glucose.

IL-1β ELISA Assay and Statistical Methods

IL-1β production is a standard and robust assay used for measuring NLRP3 inflammasome activation. IL-1β production was measured utilising a commercially available IL-1β ELISA assay kit (Human IL-1β ELISA MAX™ Deluxe), a validated assay platform that has been used to measure inflammasome activation (Fuchs et al., 2016; Ireland et al., 2017; Naji et al., 2016; Niemiec et al., 2017).

Absorbance data obtained from the ELISA assays was transformed into relative inhibition using Microsoft Excel. Dose-response curves and statistical analyses were generated using GraphPad Prism software. To generate dose-response curves, first the dose was transformed into $Log_{10}$, then curves were generated using the non-linear regression option log[inhibitor] vs response-variable slope (four parameter). Statistical comparisons between treatment and control groups were performed using One Way ANOVA with GraphPad Prism statistical software. Statistical significance is represented as: *=p≤0.05; =p≤0.01; * p≤0.001; and **** p≤0.0001.

Combinatorial Index (CI) Synergy Analyses

The established combination index (CI) method of Chou-Talalay was applied to assess synergy (Chou, 2002, 2006, 2008, 2010; Chou and Talalay, 1981, 1984). Dose-response experiments were performed in 96-well plates using the dose-response layout recommended for Compusyn analyses (Chou, 2005). The latest version of CompuSyn software was used to analyse data and generate CI and graphical representations of drug-drug interactions.

Example 1

Human Monocyte NLRP3 Assay Platform

The well-characterised LPS plus ATP NLRP3 inflammasome activation in human monocytes protocol was utilised (Liao et al., 2013) (Chanput et al., 2014; Xie et al., 2014) (Martirosyan et al., 2015) (Mangan et al., 2018; Mezzasoma et al., 2016). Monocytes were first primed for three hours with 100 nM LPS, then stimulated with ATP. A standard curve generated using the BioLegend human IL-1β ELISA kit is shown in FIG. 1A. The standard curve for each assay displays an $r^2$ of at least 0.98. FIG. 1B is a graph of the results of the THP-1 inflammasome assay. THP-1 monocytes were treated with 100 nM LPS for three hours, 10 mM ATP for one hour, or primed with 100 nM LPS for three hours then stimulated with 10 mM ATP for one hour to activate the NLRP3 inflammasome and release IL-1β. The final column shows THP-1 cells pre-treated with the NLRP3 inhibitor mcc950 before being stimulated with LPS and ATP.

From FIG. 1B it can be seen that THP-1 cells primed with LPS but not stimulated with ATP displayed a low but detectable level of IL-1β production, whereas the ATP-only stimulated cells did not generate any detectable IL-1β. The primed and stimulated THP-1 cells displayed maximal IL-1β response. Importantly, NLRP3 activation by LPS priming and ATP stimulation was completely abrogated by pre-treating the THP-1 cells with the specific NLRP3 inhibitor mcc950 (Coll et al., 2015).

Figure 2:
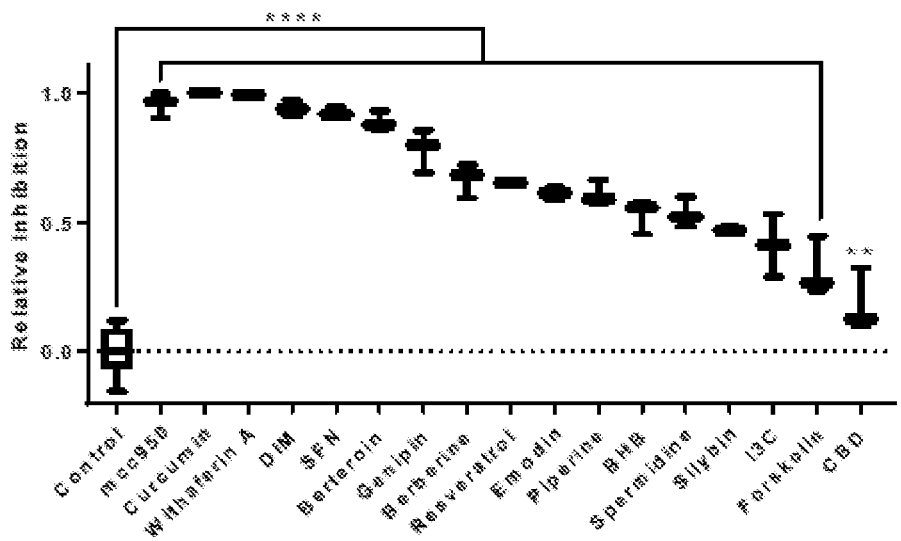
FIG. 2 is a graph of the results from a natural compound screen for inhibitors of the NLRP3 inflammasome.

The THP-1 inflammation assay was used to screen a small compound library for NLRP3 inhibitors. FIG. 2 shows the lead compounds identified in the screen that displayed significant inflammation inhibitory activity relative to the empty vehicle control.

Together, these data confirm that 1) the THP-1 NLRP3 inflammasome assay provides a suitable experimental platform to analyse inhibitors of inflammasome activation; 2)

the pure compound and plant extract dose ranges of the invention are appropriate for assessing NLRP3 inflammasome inhibition and 3) that a variety of natural compounds possess the ability to inhibit NLRP3 activation.

Figure 3:
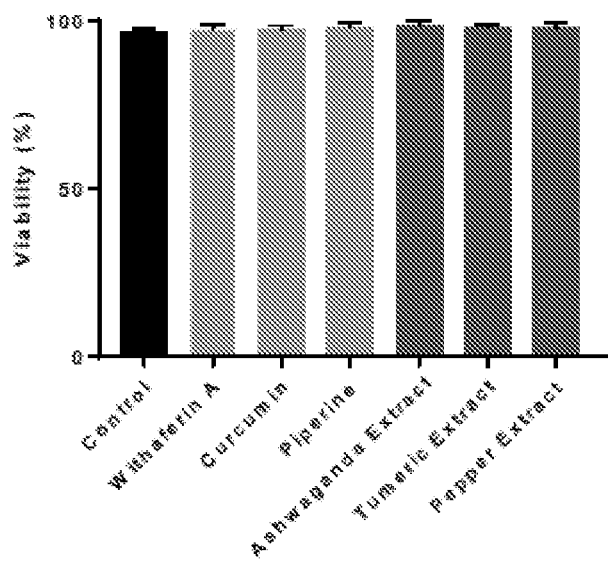
FIG. 3 is a graph showing the viability of THP-1 monocytes following five hours of incubation in the presence of empty vehicle (as a control) or various pure compounds and plant extracts.

Next, the effect on cell viability of the compounds and plant extracts of the invention was assessed. THP-1 monocytes were incubated for five hours with vehicle control (DMSO), pure compounds or plant extracts, at the maximal doses used. After five hours the cells were mixed with trypan blue and the live cells (trypan blue negative) and dead cells (trypan blue positive) assessed by light microscopy. The results are shown in FIG. 3. Specifically, the mean viability scores of at least six repeats for each treatment are shown. Comparison of the control to the treatment groups using ANOVA confirmed that there was no statistical difference between the control group and the treatment groups. Thus, the compounds and plant extracts had no detectable effect on cell viability within the time frame of the experiments.

Example 2

Single Compound Dose-Response

The focus of the present application are three compounds identified in the screen:
1. Withaferin A; a naturally occurring steroidal lactone isolated from the plant *Withania somnifera*, commonly known as ashwagandha, or Indian winter cherry. Withaferin A has been reported to display anti-inflammatory (Dubey et al., 2018), anti-tumour (McKenna et al., 2015) and inhibition cell motility, invasion and anti-angiogenesis (Lee and Choi, 2016).
2. Curcumin; the principle curcuminoid of *Curcuma longa* or turmeric (Deguchi, 2015), a natural compound with many published activities including anti-inflammatory activities (Ghosh et al., 2015).
3. Piperine; an alkaloid found in *Piper nigrum* or black pepper, a natural compound also known to have anti-inflammatory properties (Ying et al., 2013).

Figure 4:
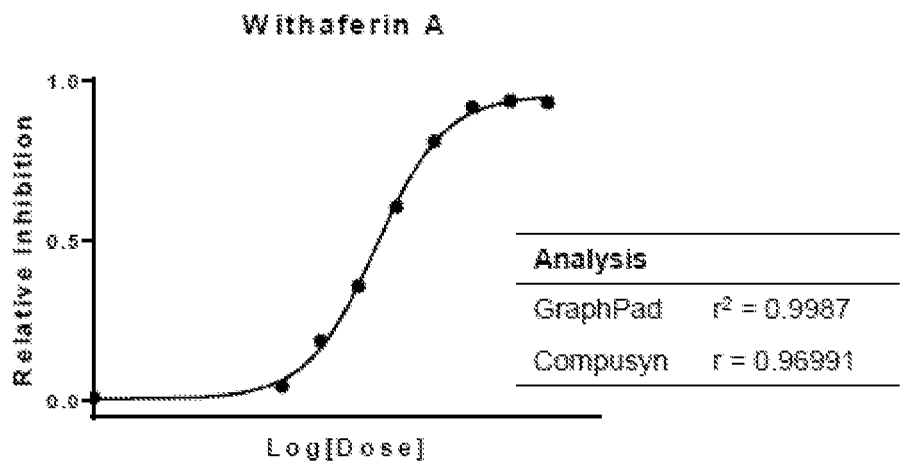
FIG. 4 is a series of dose-response curves. 3A, withaferin A; 3B, curcumin; and 3C, piperine.
Figure 4:
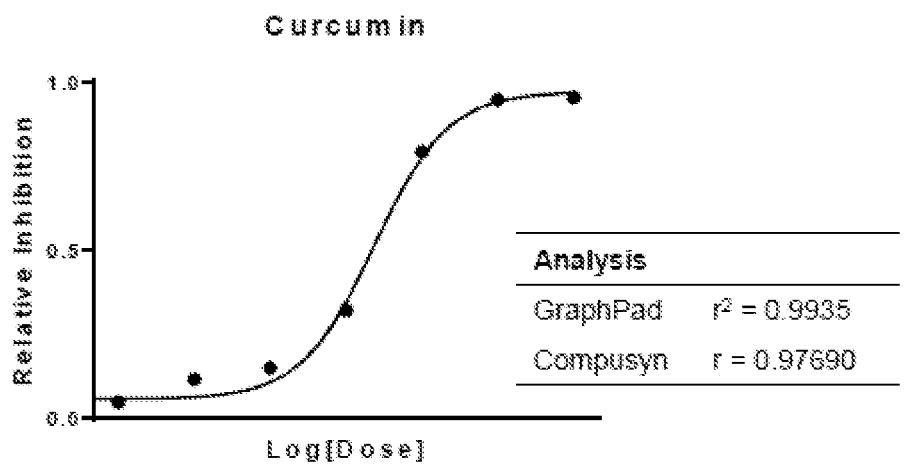
Figure 4:
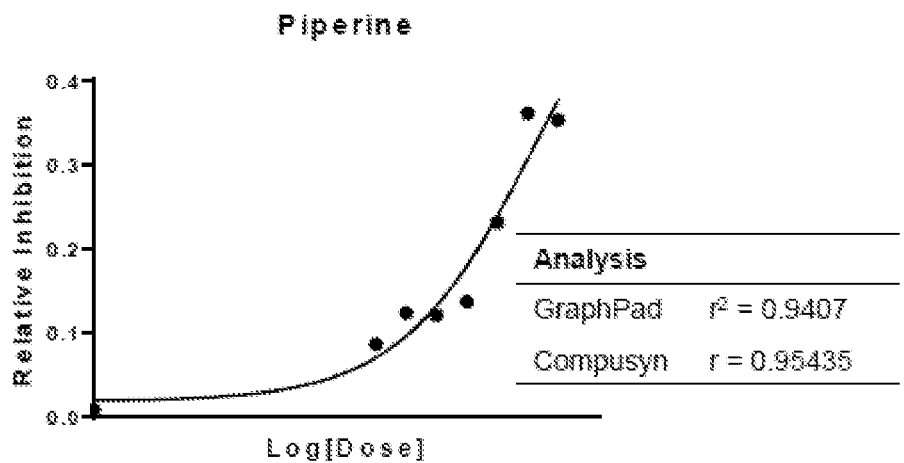

Analysis of the inflammasome inhibitory activity of these three pure compounds revealed that all three compounds generated dose-response curves that could be robustly fitted using non-linear curve functions in the Graph Pad Prism software package to $r^2$ values close to one, and with Compusyn to generate r values above 0.9. The dose-response curves for withaferin A, curcumin and piperine are shown in FIG. 4. The insert for each curve shows the r and $r^2$ values for the curve fit functions derived from the Graph Pad and Compusyn software packages.

In the assay system, piperine came out of solution at the higher doses, and thus inflammasome inhibition above approximately 35% using this compound was not observed. Nevertheless, all three compounds generated dose-response curves of sufficient quality to fulfil the pre-requisites required for further drug combination studies, namely the accurate determination of the individual drug potency and the generation of high quality dose-response curves with r>0.9 (Chou, 2006, 2008, 2010; Chou and Talalay, 1984).

Collectively, these data confirm that the three compounds, withaferin A, curcumin and piperine, inhibit NLRP3 inflammasome activity, and that the dose-response curves obtained in the experimental system are of sufficient quality to permit a formal analysis of drug combination effects using the established combinatorial index (CI) methodology.

Figure 5:
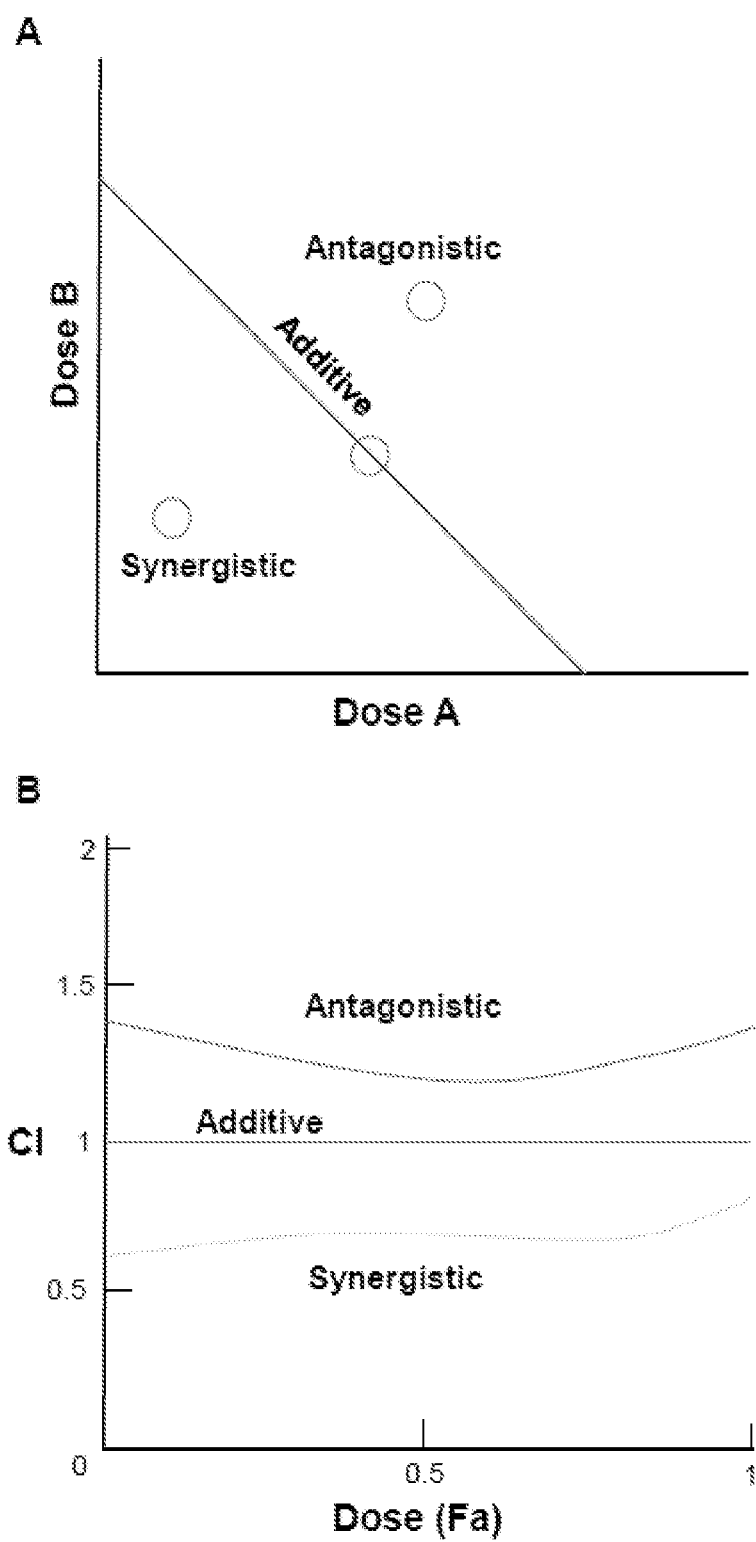
FIG. 5A is an illustrative example of an idealised isobologram used to assess synergy at a specific dose.
FIG. 5B is an illustrative example of a CI plot used to assess synergy across all dose ranges.

Two graphical representations of CI analyses are used throughout. As a result of using constant ratio combinations, normalised isobolograms could be generated from Compusyn. In a normalised isobologram, each hypotenuse represents one dose (e.g. Fa 0.5) with data points on the lower left of the hypotenuse representing synergism, data-points on the upper right of the hypotenuse representing antagonism, and data-points on the hypotenuse representing an additive effect at that dose range (FIG. 5A). To graphically present synergy across all dose ranges, CI plots were used, where the CI value is presented on the Y axis and the dose (Fa) on the X axis. Data points and simulated curves below CI=1 (horizontal line) represent synergism, data points and simulated curves above CI=1 represent antagonism, and data points and simulated curves on CI=1 represent an additive effect (FIG. 5B).

Example 3

Withaferin A and Curcumin

Figure 6:
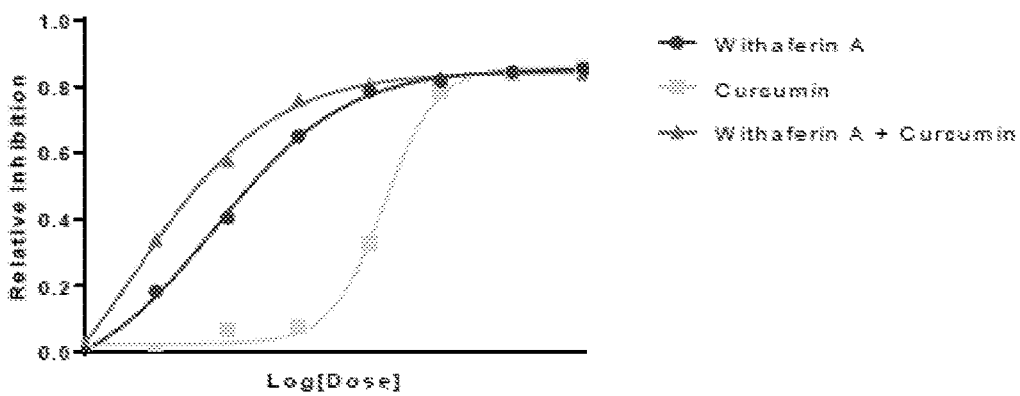
FIG. 6A is a series of dose-response curves for withaferin A, curcumin, and withaferin A in combination with curcumin.
FIG. 6B is a series of isobolograms of the combination of withaferin A and curcumin at various low dose ranges.
FIG. 6C is a combination index (CI) plot for withaferin A and curcumin.
Figure 6:
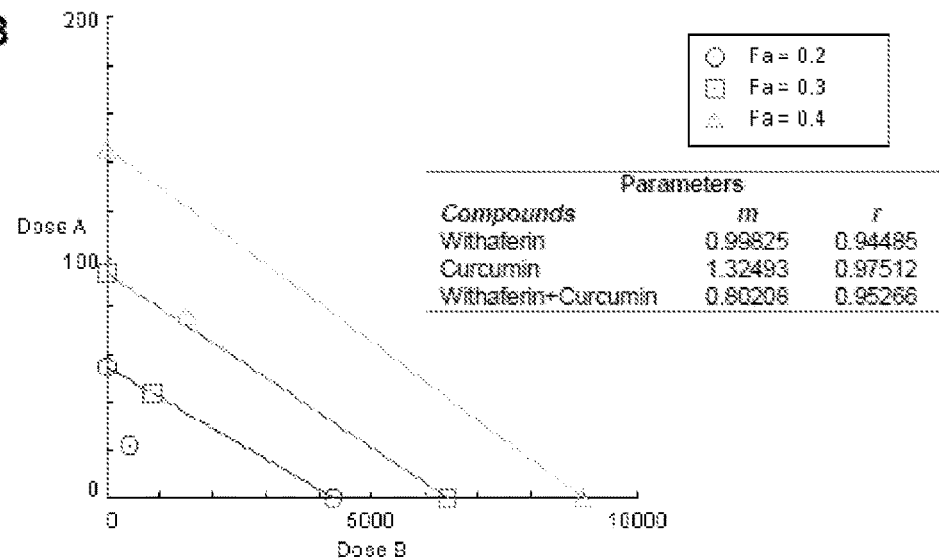
Figure 6:
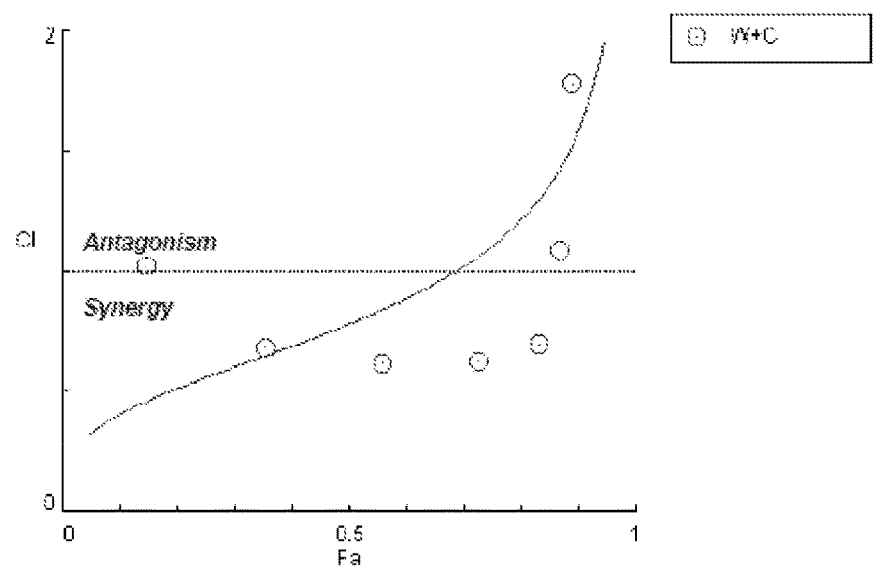

The effect of combining withaferin A with curcumin was investigated. Dose-response curves for the single compounds withaferin A and curcumin, and for the combination of withaferin A and curcumin are shown in FIG. 6A. Comparison of these dose-response curves shows that the combination of withaferin A plus curcumin displays greater efficacy than either compound alone.

As synergistic, additive and even antagonistic compounds can yield improved efficacy in combination (Chou, 2010), the drug-drug interactions between withaferin A and curcumin were formally assessed using the combinatorial index (CI) analysis. As shown in the isobolograms in FIG. 6B, withaferin A and curcumin is synergistic within the low dose ranges, Fa 0.2, Fa 0.3, and Fa 0.4. The inset of FIG. 6B shows the Compusyn m and r values for the single and combined dose-response curves used to generate the CI analysis.

A complete analysis of the CI across all dose ranges, as set out in Table 2, reveals that withaferin A and curcumin are synergistic at doses up to Fa 0.7. From FIG. 6C, which is a graph of the CI for withaferin A combined with curcumin across the entire range of concentrations, it can be seen that at doses above Fa 0.7 the interaction between withaferin A and curcumin becomes increasingly antagonistic.

TABLE 2

Summary of the CI data for pure withaferin A, curcumin and piperine

| | Combinatorial Index (CI) | | |
|---|---|---|---|
| Fa | withaferin A + curcumin | withaferin A + piperine | curcumin + piperine |
| 0.05 | 0.32845 | 0.71984 | 0.64258 |
| 0.1 | 0.40626 | 0.68239 | 0.62536 |
| 0.15 | 0.46454 | 0.67879 | 0.62588 |
| 0.2 | 0.51455 | 0.68287 | 0.63077 |
| 0.25 | 0.56039 | 0.68969 | 0.63731 |
| 0.3 | 0.60419 | 0.69774 | 0.64469 |
| 0.35 | 0.6473 | 0.70652 | 0.65261 |
| 0.4 | 0.69079 | 0.71583 | 0.661 |
| 0.45 | 0.73558 | 0.72564 | 0.66987 |
| 0.5 | 0.78265 | 0.73602 | 0.6793 |
| 0.55 | 0.83314 | 0.74707 | 0.68942 |
| 0.6 | 0.88847 | 0.759 | 0.70042 |
| 0.65 | 0.95062 | 0.77208 | 0.71259 |
| 0.7 | 1.02251 | 0.78672 | 0.72634 |
| 0.75 | 1.10883 | 0.80358 | 0.74233 |
| 0.8 | 1.21788 | 0.82377 | 0.76169 |
| 0.85 | 1.36642 | 0.8494 | 0.78657 |
| 0.9 | 1.59628 | 0.88533 | 0.82194 |

TABLE 2-continued

Summary of the CI data for pure withaferin
A, curcumin and piperine

| | Combinatorial Index (CI) | | |
|---|---|---|---|
| Fa | withaferin A + curcumin | withaferin A + piperine | curcumin + piperine |
| 0.95 | 2.06544 | 0.9477 | 0.88452 |
| 0.97 | 2.49363 | 0.99526 | 0.93306 |

CI values < 1 indicate synergy, CI = 1 indicate an additive effect, and CI > 1 indicate antagonism.

In summary, the CI analysis of the combination of withaferin A and curcumin reveals that the two compounds are synergistic within the low dose ranges that are the focus of this invention.

Example 4

Withaferin A and Piperine

Figure 7:
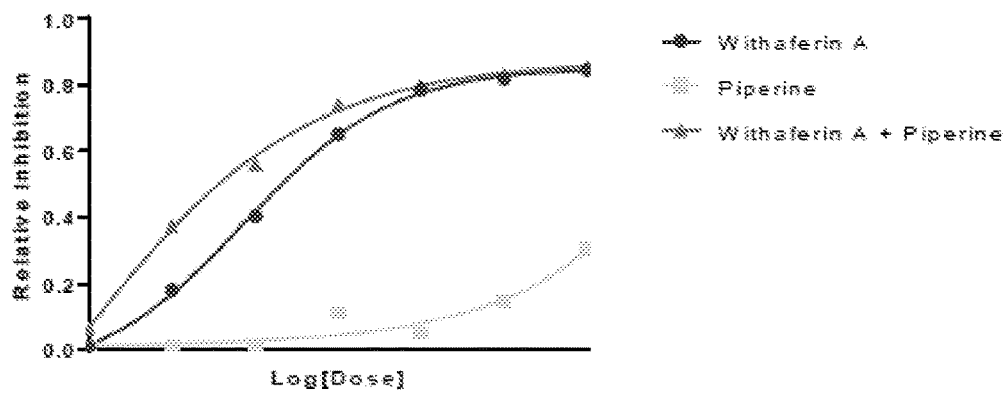
FIG. 7A is a series of dose-response curves for withaferin A, piperine, and withaferin A in combination with piperine.
FIG. 7B is a series of isobolograms of the combination of withaferin A and piperine at various low dose ranges.
FIG. 7C is a combination index (CI) plot for withaferin A and piperine.
Figure 7:
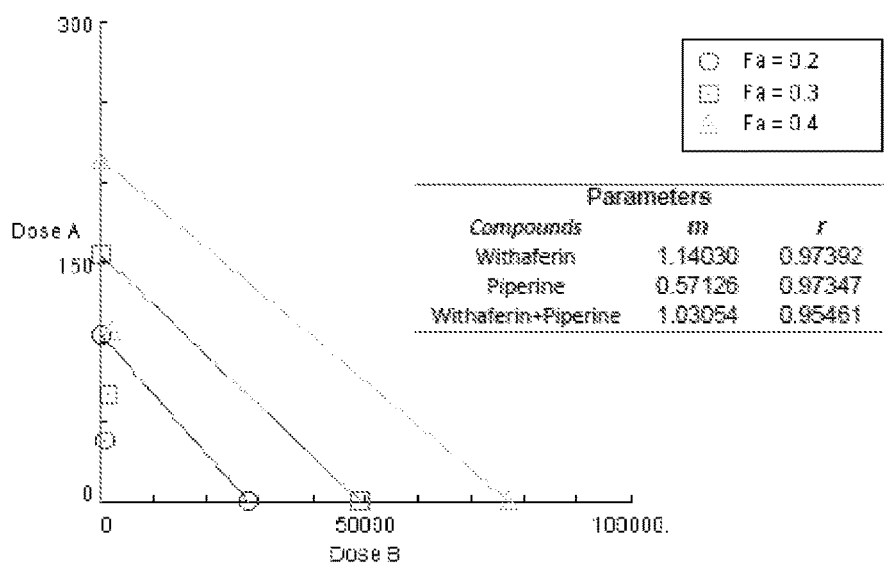
Figure 7:
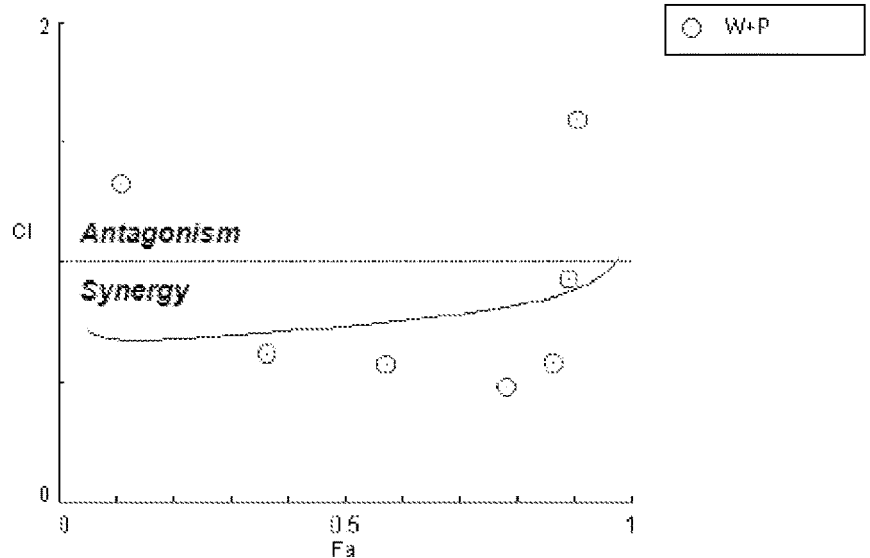

The drug interaction between withaferin A and piperine was investigated. Dose-response curves for the single compounds withaferin A and piperine, and for the combination of withaferin A and piperine are shown in FIG. 7A. Comparison of the dose-response curves confirms that the combination of withaferin A and piperine is more efficacious than either compound alone, especially within the low dose-range of interest. The drug-drug interactions between withaferin A and piperine were formally assessed using combinatorial index (CI) analysis. As shown in the isobolograms in FIG. 7B, withaferin A and piperine is synergistic within low dose ranges (Fa 0.2, Fa 0.3 and Fa 0.4). The inset of FIG. 7B shows the Compusyn m and r values for the single and combined dose-response curves used to generate the CI analysis.

A complete assessment of the CI across all dose ranges, as set out in Table 2, reveals that withaferin A and piperine are synergistic across all the doses tested. FIG. 7C is a graph of the CI for withaferin A combined with piperine across the entire range of concentrations.

In summary, the CI analysis of the combination of withaferin A and piperine reveals that the two compounds are synergistic across all doses tested. Importantly, withaferin A and piperine are synergistic within the low dose ranges that are the focus of this invention.

Example 5

Curcumin and Piperine

Figure 8:
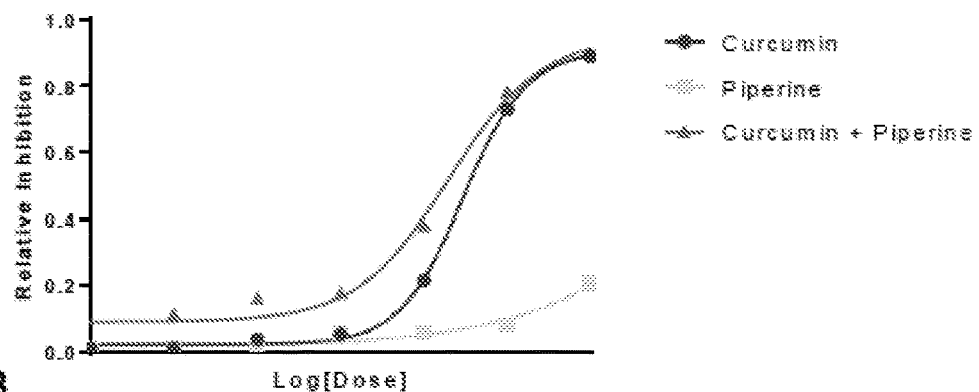
FIG. 8A is a series of dose-response curves for curcumin, piperine, and curcumin in combination with piperine.
FIG. 8B is a series of isobolograms of the combination of curcumin and piperine at various low dose ranges.
FIG. 8C is a combination index (CI) plot for curcumin and piperine.
Figure 8:
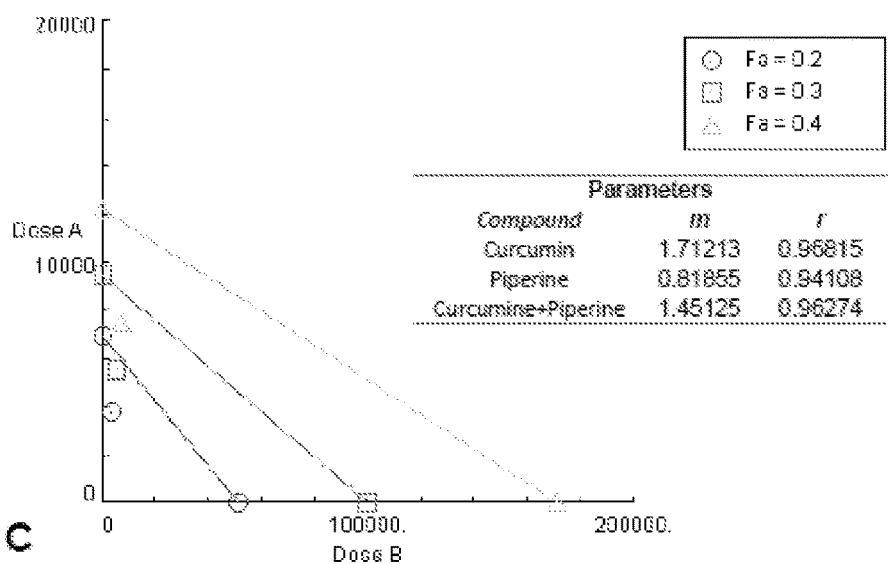
Figure 8:
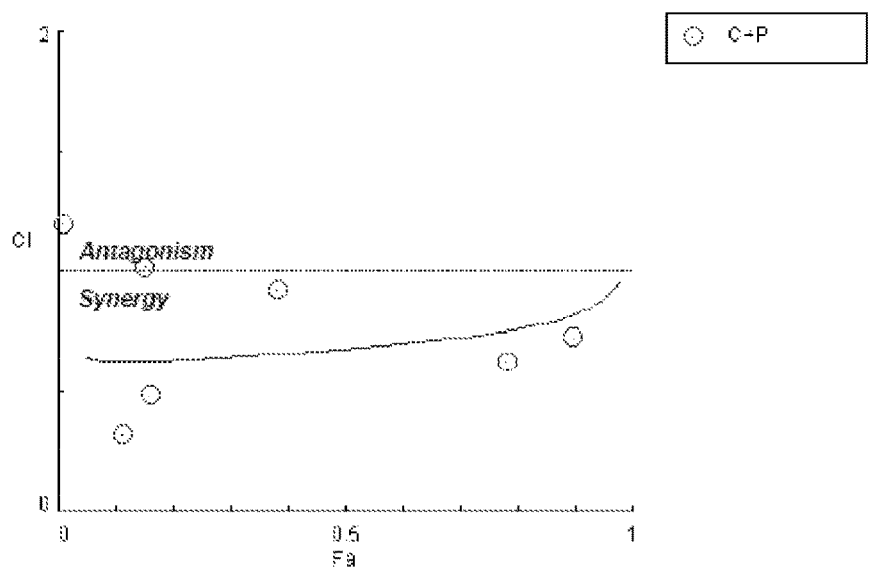

The drug interaction between curcumin and piperine was investigated. Dose-response curves for the single compounds curcumin and piperine, and for the combination of curcumin and piperine are shown in FIG. 8A. Comparison of the dose-response curves confirms that the combination of curcumin and piperine is more efficacious than either compound alone, which was particularly striking within the low dose-range. The drug-drug interactions between curcumin and piperine were formally assessed using combinatorial index (CI) analysis. As shown in the isobolograms in FIG. 8B, curcumin and piperine are synergistic within low dose ranges (Fa 0.2, Fa 0.3 and Fa 0.4). The inset of FIG. 6B shows the Compusyn m and r values for the single and combined dose-response curves used to generate the CI analysis.

Assessing the CI across all dose ranges, as set out in Table 2, reveals that curcumin and piperine are synergistic across all dose ranges tested. FIG. 8C is a graph of the CI for curcumin combined with piperine across the entire range of concentrations.

In summary, the CI analysis of the combination of curcumin and piperine reveals that the two compounds are synergistic across all doses tested. Importantly, curcumin and piperine are synergistic within the low dose ranges that are the focus of this invention.

Example 6

Statistical Analysis of Withaferin A, Curcumin and Piperine Combinations

Having determined that withaferin A, curcumin and piperine are synergistic at low doses, the significance of the improved efficacy of drug combinations relative to their cognate single compounds within the low dose range was determined. In order to obtain statistically significant drug treatments, THP-1 cells were treated using compounds at dose ranges below Fa 0.4 with multiple experimental replicates, with the statistical significance between the different experimental groups assessed using ANOVA.

FIGS. 9A-9C are graphs showing a statistical comparison of the efficacy of combinations of compounds and single compounds. 9A, withaferin A and curcumin; 9B, withaferin A and piperine; and 9C, curcumin and piperine. FIG. 9D is a graph showing the viability of THP-1 monocytes in the presence of empty vehicle (as a control) or the compound combinations at the highest concentration of interest.

Figure 9:
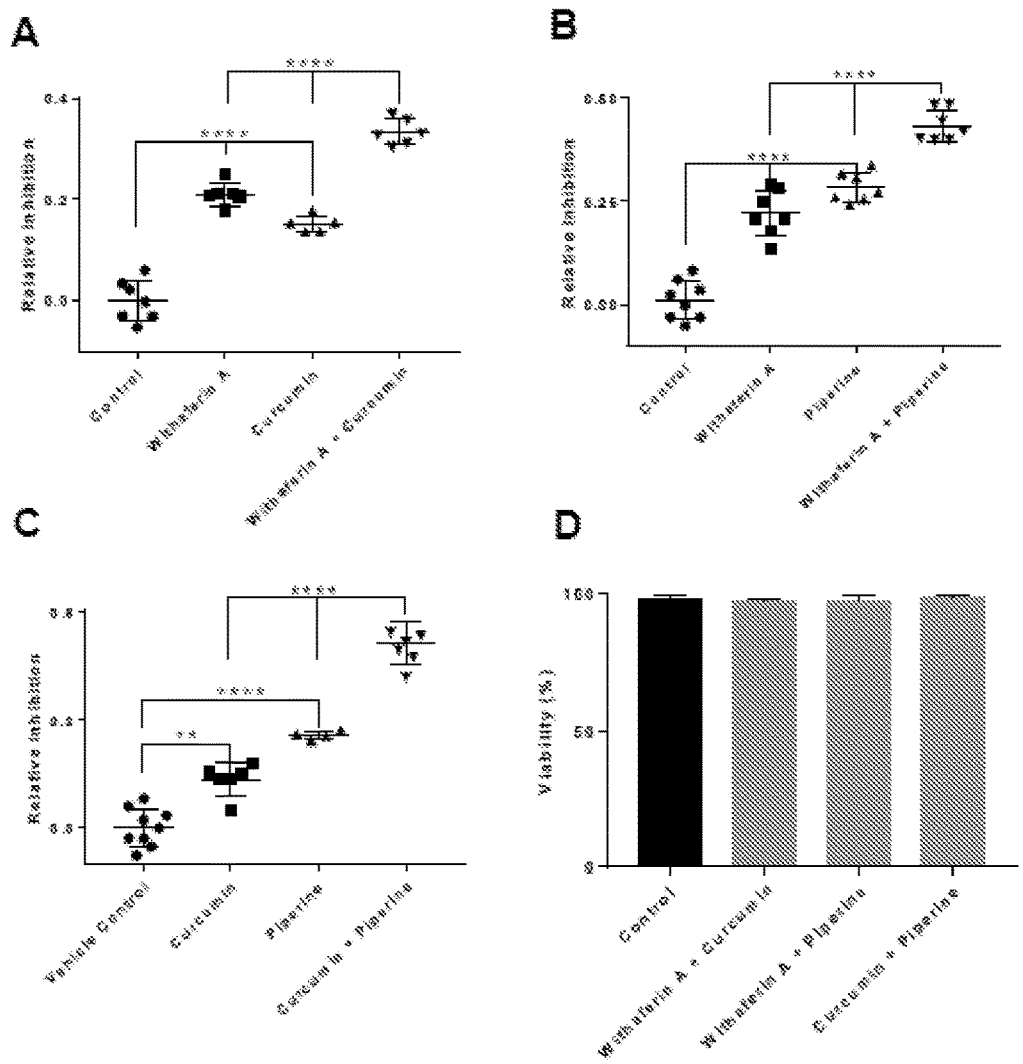
FIGS. 9A-9C are graphs showing a statistical comparison of the efficacy of combinations of compounds and single compounds. 9A, withaferin A and curcumin; 9B, withaferin A and piperine; and 9C, curcumin and piperine.
FIG. 9D is a graph showing the viability of THP-1 monocytes in the presence of empty vehicle (as a control) or the compound combinations at the highest concentration of interest.

From the data in FIG. 9, withaferin A and curcumin as single compounds were efficacious relative to vehicle control ($p<0.0001$). Critically, the combination of curcumin plus withaferin A was more efficacious than either compound alone, a conclusion supported with high statistical significance ($p<0.0001$) (FIG. 9A). Withaferin A and piperine as single compounds were efficacious relative to the vehicle treated control ($p<0.0001$), and the dug combination of withaferin A plus piperine was more efficacious than either of the compounds alone ($p<0.0001$) (FIG. 9B). Curcumin and piperine as single compounds displayed efficacy relative to the vehicle control with statistical significance for curcumin ($p<0.01$) and high statistical significance for piperine ($p<0.0001$). Importantly, curcumin and piperine in combination displayed increased efficacy relative to single compounds alone, with high statistical significance ($p<0.0001$) (FIG. 9C).

Next, how the drug combinations affected THP-1 cell viability was assessed. Multiple replicates of THP-1 cells were treated with empty vehicle (control), or two-compound drug combinations with each compound at a dose of Fa 0.5, i.e. a dose above that tested in the compound efficacy combination experiments. After five hours, cell viability was assessed using Trypan Blue exclusion to identify viable cells. The results are shown in FIG. 9D. No significant difference was observed between the control and the drug-treated cells, indicating that the two-compound drug treatments had no effect on cell viability under our experimental conditions.

In conclusion, all three combinations (withaferin A plus curcumin, withaferin A plus piperine, and curcumin plus piperine) were significantly more efficacious than their cognate single compound controls, with no effect on cell viability.

Example 7

Drug-Drug Interactions Between Withaferin A, Curcumin and Piperine

Figure 10:
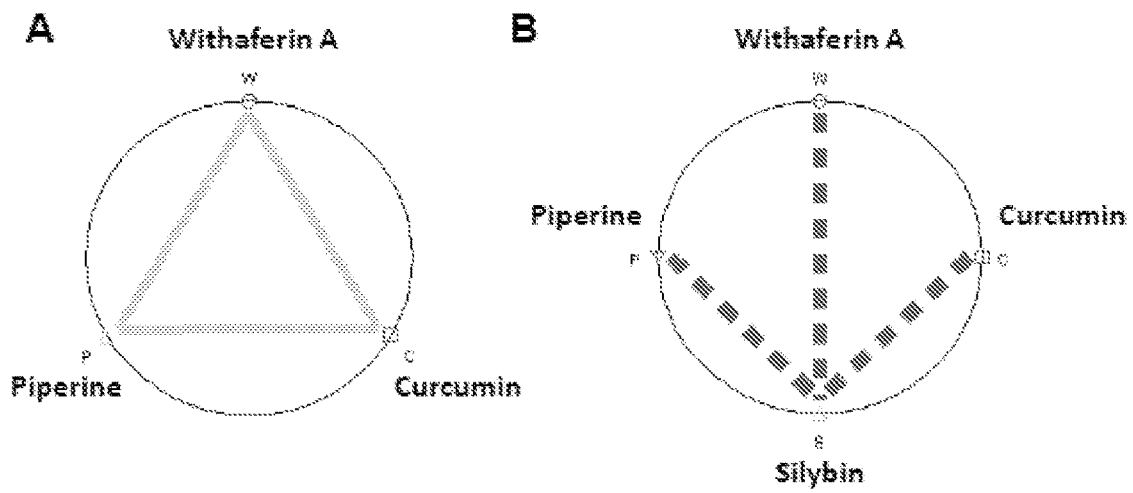
FIG. 10A is a polynonogram showing the compound interactions between withaferin A, curcumin and piperine.
FIG. 10B is a polynonogram showing the compound interactions between silybin, piperine, curcumin and withaferin A.

A polynonogram is a graphical representation depicting synergism (solid green line), additive effect (thin green line) and antagonism (dashed red line). The thickness of the line represents the degree of synergism or antagonism. A synergy analysis with all three compounds compared within a single experiment was undertaken to generate a polynonogram that summarises the synergistic interaction between the three pure compounds withaferin A, curcumin and piperine (FIG. 10A). This summary supports the finding that all three compounds have synergistic interactions within the dose range of interest.

It is important to note that the majority of anti-inflammatory compounds identified in the preliminary screen were found to be antagonistic when tested in drug combination experiments. For example silybin, a known NLRP3 inhibitor (Zhang et al., 2018), was identified as a lead compound in the primary screen. Despite effectively inhibiting inflammation as a single compound, silybin displayed striking antagonism when combined with withaferin A, curcumin and piperine, as shown in FIG. 10B.

The data indicate that synergistic interactions appear to be the exception rather than the norm for natural compound combinations. Discovering two synergistic compounds is rare, and discovering three natural compounds that are synergistic in combination is highly improbable and therefore by definition unexpected. Synergy between natural compounds cannot be predicted from historical data, but must be discovered and validated through systematic, empirical drug combination experiments and analysis.

Example 8

Combination of Ashwagandha and Turmeric Plant Extracts

Having identified promising synergistic interactions between the natural compounds withaferin A, curcumin and piperine, plant extracts rich in in these compounds were studied. Ashwagandha (*Withania somniferia*) is rich in withaferin A, turmeric (*Curcuma longa*) is a natural source of curcumin, and the black pepper (*Piper nigrum*) plant is the natural source of piperine.

Figure 11:
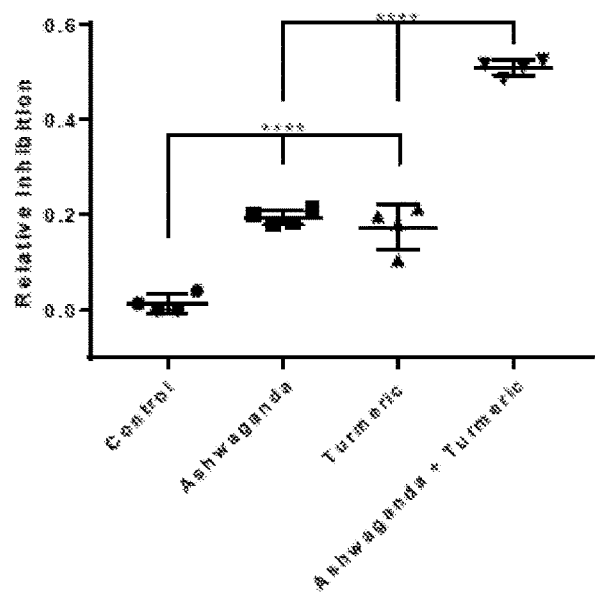
FIG. 11A is a graph of a statistical comparison of the efficacy of extracts of ashwagandha and turmeric, and a combination of extracts of ashwagandha and turmeric.
FIG. 11B is a comparison of the mean relative inhibition of the treatment groups of FIG. 11A.
FIG. 11C is a graph of a statistical comparison of the efficacy of extracts of ashwagandha and turmeric, and a combination of extracts of ashwagandha and turmeric, as in FIG. 11A, except that the concentration of the turmeric extract was not significantly different to that of the vehicle control.
Figure 11:
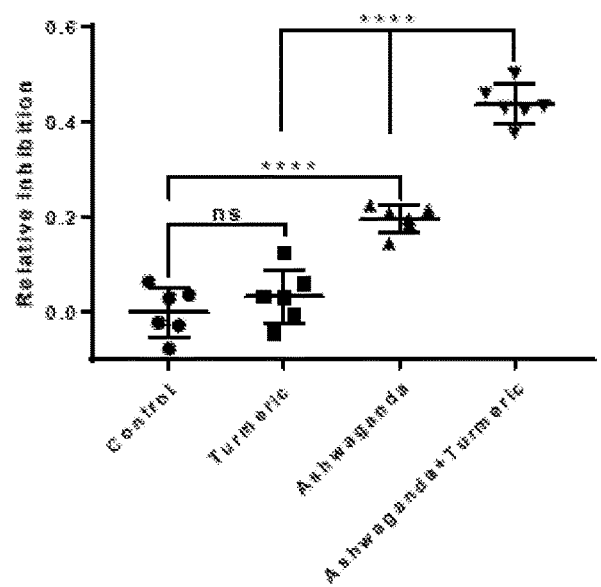

The interaction between ashwagandha and turmeric plant extracts was studied. Turmeric plant extract presented an experimental challenge because the active ingredients precipitated at higher doses, making generation of robust dose-response curves for turmeric extract impossible using our cell-based assay system. To overcome this experimental limitation low doses at approximately the Fa 0.2 range were focused on, and the mean relative inhibition values of the single extract versus the ashwagandha plus turmeric plant extract combination were compared. FIG. 11A is a graph of a statistical comparison of the efficacy of extracts of ashwagandha and turmeric, and a combination of extracts of ashwagandha and turmeric. The data indicates that the single plant extracts inhibited inflammasome activity in monocytes significantly relative to the vehicle control (p<0.0001), whilst the combination of ashwagandha and turmeric extract was more efficacious than the single extracts. This difference also reached high significance (p<0.0001).

Comparison of the mean relative inhibition of the single extracts versus the extract combination, as shown in FIG. 11B, reveals that the efficacy of the ashwagandha plus turmeric combination was more than additive.

In one experiment, a turmeric extract dose that was too low, Fa approximately 0, to effectively inhibit inflammation in the stimulated cells as a single compound was used (FIG. 11C). Nevertheless, this turmeric extract dose potentiated the ability of the ashwagandha extract to inhibit inflammation by a factor of approximately two (p<0.0001) (FIG. 11C).

In conclusion, these data show that at low doses ashwagandha and turmeric plant extracts inhibit inflammation with an efficacy that is more-than-additive at low doses. Moreover, turmeric plant extract has the ability to potentiate the efficacy of ashwagandha extract at doses where the turmeric extract displays no activity as a single compound.

Example 9

Combination of Turmeric and Pepper Extracts

Figure 12:
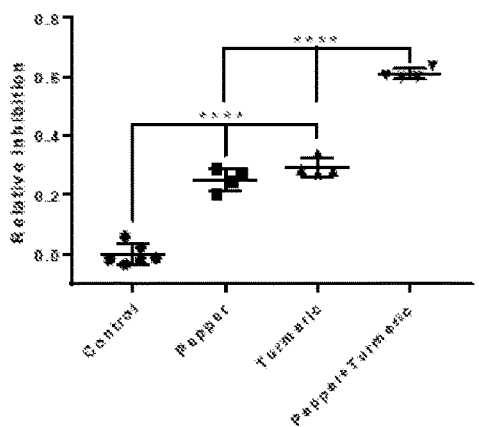
FIG. 12A is a graph of a statistical comparison of the efficacy of extracts of pepper and turmeric, and a combination of extracts of pepper and turmeric.
FIG. 12B is a comparison of the mean relative inhibition of the treatment groups of FIG. 12A.

The combination of turmeric and pepper (*Piper nigrum*) plant extracts was investigated. The pepper plant extracts displayed very low solubility in aqueous solution, again preventing the generation of high-quality dose-response curves for pepper. The experiments were thus constrained to low doses of pepper extract where the active ingredients remained in solution (within the Fa 0.2 range). FIG. 12A is a graph of a statistical comparison of the efficacy of extracts of pepper and turmeric, and a combination of extracts of pepper and turmeric. From FIG. 12A, it can be seen that the individual extracts displayed significant inhibitory properties (p<0.0001), and the combination of turmeric and pepper extract was significantly more efficacious than the pepper or turmeric single extract treatments (p<0.0001).

FIG. 12B is a comparison of the mean relative inhibition of the treatment groups of FIG. 10A. FIG. 12B reveals that the combined effect of pepper and turmeric was more than additive compared to the single compound extracts.

Together, these data show that at low doses, turmeric and pepper plant extracts significantly inhibit NLRP3 inflammasome activity and the two extracts in combination display an efficacy that is more than additive at low doses.

Example 10

Combination of Ashwagandha and Pepper Extracts

Figure 13:
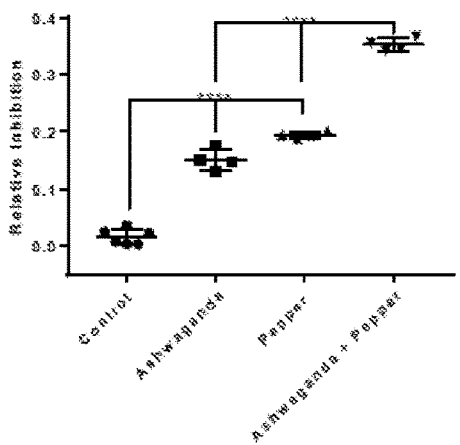
FIG. 13A is a graph of a statistical comparison of the efficacy of extracts of ashwagandha and pepper, and a combination of extracts of ashwagandha and pepper.
FIG. 13B is a comparison of the mean relative inhibition of the treatment groups of FIG. 13A.

The combination of ashwagandha and black pepper extracts was tested. Again, the focus was on assessing low doses within the Fa 0.2 range due to the solubility issues inherent to the pepper plant extract. FIG. 13A is a graph of a statistical comparison of the efficacy of extracts of ashwagandha and pepper, and a combination of extracts of ashwagandha and pepper. The data show that the single plant extracts inhibited inflammasome activation relative to the vehicle control with high significance (p<0.0001), and the extract combination displayed increased efficacy relative to the single extracts that reached high statistical significance (p<0.0001).

Comparing the mean relative inhibition of the combined extracts versus the sum of the individual extracts, as shown in FIG. 13B, reveals that the efficacy of the extract combination was more than additive.

These data show that, at low doses, the combination of ashwagandha and pepper plant extracts significantly inhibit NLRP3 inflammasome activity, and that the two extracts in combination display an efficacy that is greater than additive.

A summary of the drug-drug interactions between the pure compounds and their cognate plant extracts is set out in Table 3.

TABLE 3

Summary of Drug-Drug Interactions

| Compound Class | Combination | Interaction | Improved Efficacy compared to single compounds? |
|---|---|---|---|
| pure | withaferin A + curcumin | synergistic | yes, highly significant ($p < 0.0001$) |
| | withaferin A + piperine | synergistic | yes, highly significant ($p < 0.0001$) |
| | curcumin + piperine | synergistic | yes, highly significant ($p < 0.0001$) |
| plant extract | ashwagandha + turmeric | more than additive | yes, highly significant ($p < 0.0001$) |
| | ashwagandha + pepper | more than additive | yes, highly significant ($p < 0.0001$) |
| | turmeric + pepper | more than additive | yes, highly significant ($p < 0.0001$) |

Example 11

Efficacy of Triple Plant Extract Combination

Figure 14:
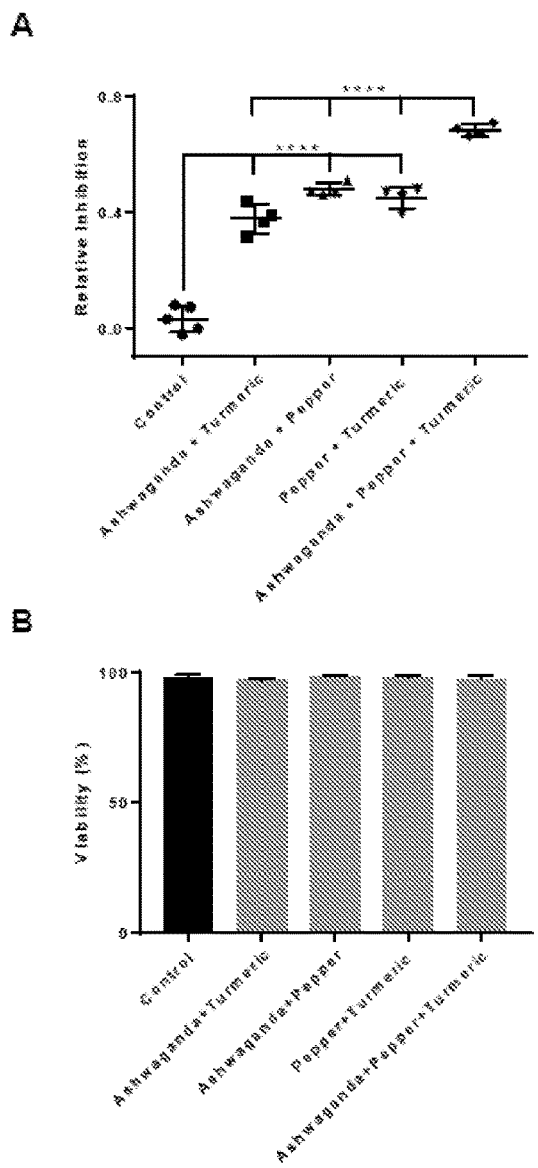
FIG. 14A is a graph of a statistical comparison of the efficacy of extracts of ashwagandha, turmeric and pepper, in double and triple combinations.
FIG. 14B is a graph showing the viability of THP-1 monocytes in the presence of empty vehicle (as a control) or the double and triple combinations of FIG. 14A using the dose conditions of FIG. 14A.

The efficacy of two-compound combinations to all three compounds in combination was compared. Again, the focus was on low dose ranges (approximately Fa 0.2 for each compound) due to the low solubility of turmeric and pepper plant extracts in aqueous solutions. FIG. 14A a graph of a statistical comparison of the efficacy of extracts of ashwagandha, turmeric and pepper, in double and triple combinations. From the data in FIG. 14A, it can be seen that all extract combinations, namely ashwagandha plus turmeric, ashwagandha plus pepper, and turmeric plus pepper, were effective at inhibiting inflammation. Specifically, the double combinations were significantly more efficacious than the vehicle control (p<0.0001). Importantly, the triple combination of ashwagandha, turmeric and pepper extracts was significantly more efficacious than the double compound combinations (p<0.0001).

The effect of the double and triple extract combinations on cell viability were tested using the Trypan Blue viability assay, with the results shown in FIG. 14B. As can be seen, neither the double nor the triple extract combinations had any significant effect on cell viability.

In summary, the combined effect of ashwagandha, turmeric and pepper extracts was significantly more efficacious then the double compound combinations, and had no effect on cell viability.

Example 12

Omega-3 Fatty Acid Supplementation

The ability of omega-3 fatty acids to inhibit inflammation was tested. Human and animal studies have revealed that supplementation with omega-3 fatty acids inhibits inflammation and may have a beneficial effect in treating inflammatory disease (Fritsche, 2006; Zhang and Spite, 2012). The omega-3 fatty acids, eicosapentaenoic acid (EPA) and docosahexaenoic acid (DHA), are known to inhibit NLRP3 activation (Yan et al., 2013). As omega-3 fatty acids share a common mechanism for inhibiting NLRP3 activation, i.e. via the activation of autophagy (Shen et al., 2017; Williams-Bey et al., 2014), DHA was chosen as the representative omega-3 fatty acid in the following experiments.

Figure 15:
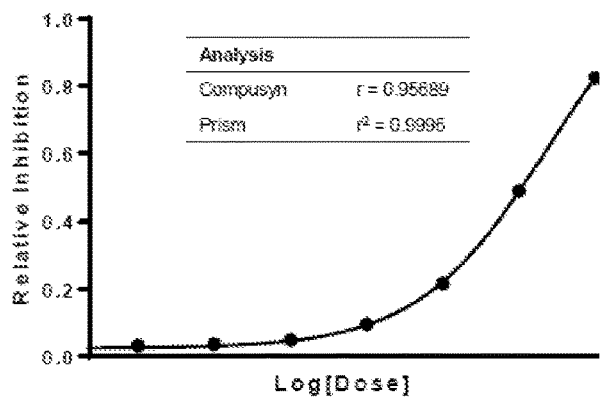
FIG. 15 is a dose-response curve of THP-1 cells treated with increasing doses of docosahexaenoic acid (DHA).

The ability of DHA as a single agent to inhibit NLRP3 activation was tested. FIG. 15 shows that DHA inhibits NLRP3 activity, generating a dose-response curve that is robustly fitted using both Compusyn and GraphPad Prism software, generating r and $r^2$ values that were close to 1.

Example 12A

Combination of DHA and Withaferin A

Figure 16:
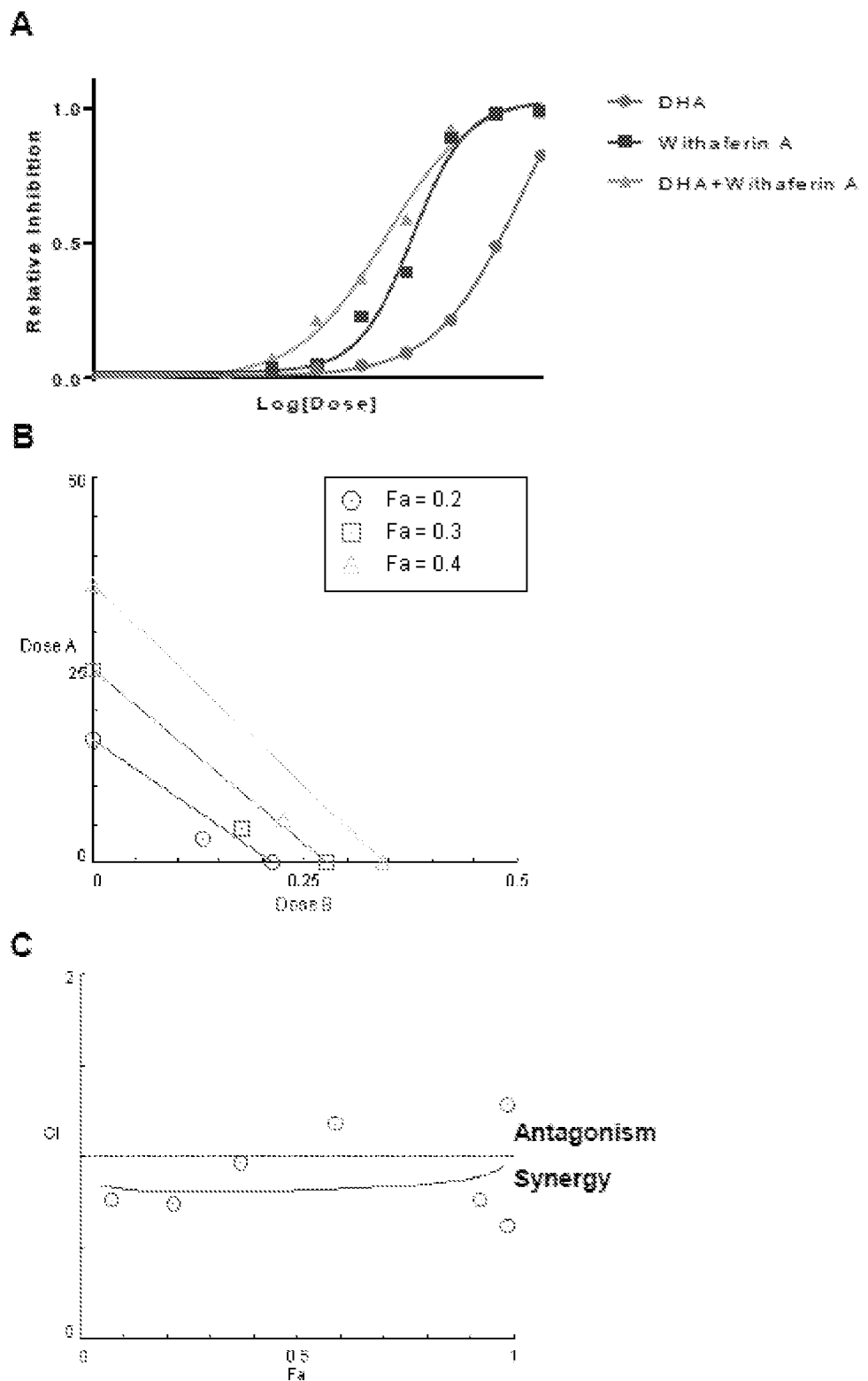
FIG. 16A is a series of dose-response curves of THP-1 cells treated with increasing doses of DHA, withaferin A, and DHA plus withaferin A.
FIG. 16B is a series of isobolograms of THP-1 cells treated with DHA and pure withaferin A at low doses.
FIG. 16C is a CI plot of THP-1 cells treated with DHA and withaferin A across the entire dose range.

The combination of DHA and withaferin A to inhibit NLRP3 activation was tested. The dose-response curves shown in FIG. 16A reveal that the combination of DHA plus withaferin A is more efficacious than DHA alone and withaferin A alone.

The drug-drug interaction between DHA and withaferin A was formally assessed using CI analysis. As shown in the isobolograms in FIG. 16B, within the low dose ranges that are the focus of this application, DHA is synergistic with withaferin A. The combinatorial plot shown in FIG. 16C and the CI values summarised in Table 4 show that DHA and withaferin A are synergistic across all effective dose ranges.

Example 12B

Combination of DHA and Curcumin

Figure 17:
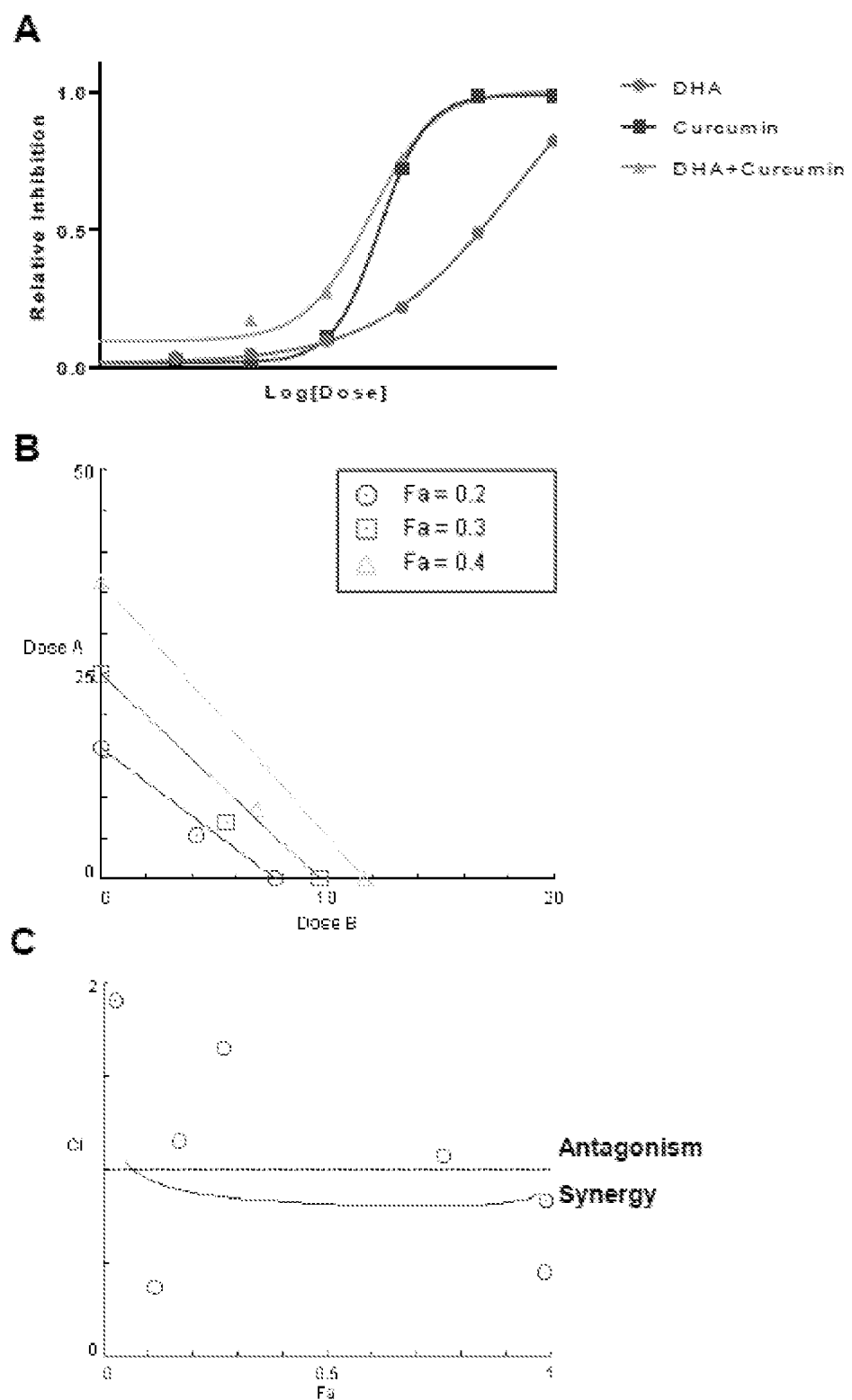
FIG. 17A is a series of dose-response curves of THP-1 cells treated with increasing doses of DHA, curcumin, and DHA combined with curcumin.
FIG. 17B is a series of isobolograms of THP-1 cells treated with DHA and curcumin at low doses.
FIG. 17C is a CI plot of THP-1 cells treated with DHA and curcumin across the entire dose range.

The effect of the combination of DHA and curcumin inhibitors on NLRP3 inflammasome activity was tested. The dose-response curves shown in FIG. 17A reveal that the combination of DHA and curcumin is more efficacious than the single compounds, particularly within the low dose ranges that are the focus of this application.

The drug-drug interaction between DHA and curcumin was formally assessed using CI analysis. As shown in the isobolograms in FIG. 17B, DHA and curcumin are synergistic within the dose ranges between Fa 0.4 to Fa 0.2. The CI plot in FIG. 17C and CI values summarised in Table 4 reveal that the interaction between DHA and curcumin is synergistic across all effective dose ranges.

Example 12C

Combination of DHA and Piperine

Figure 18:
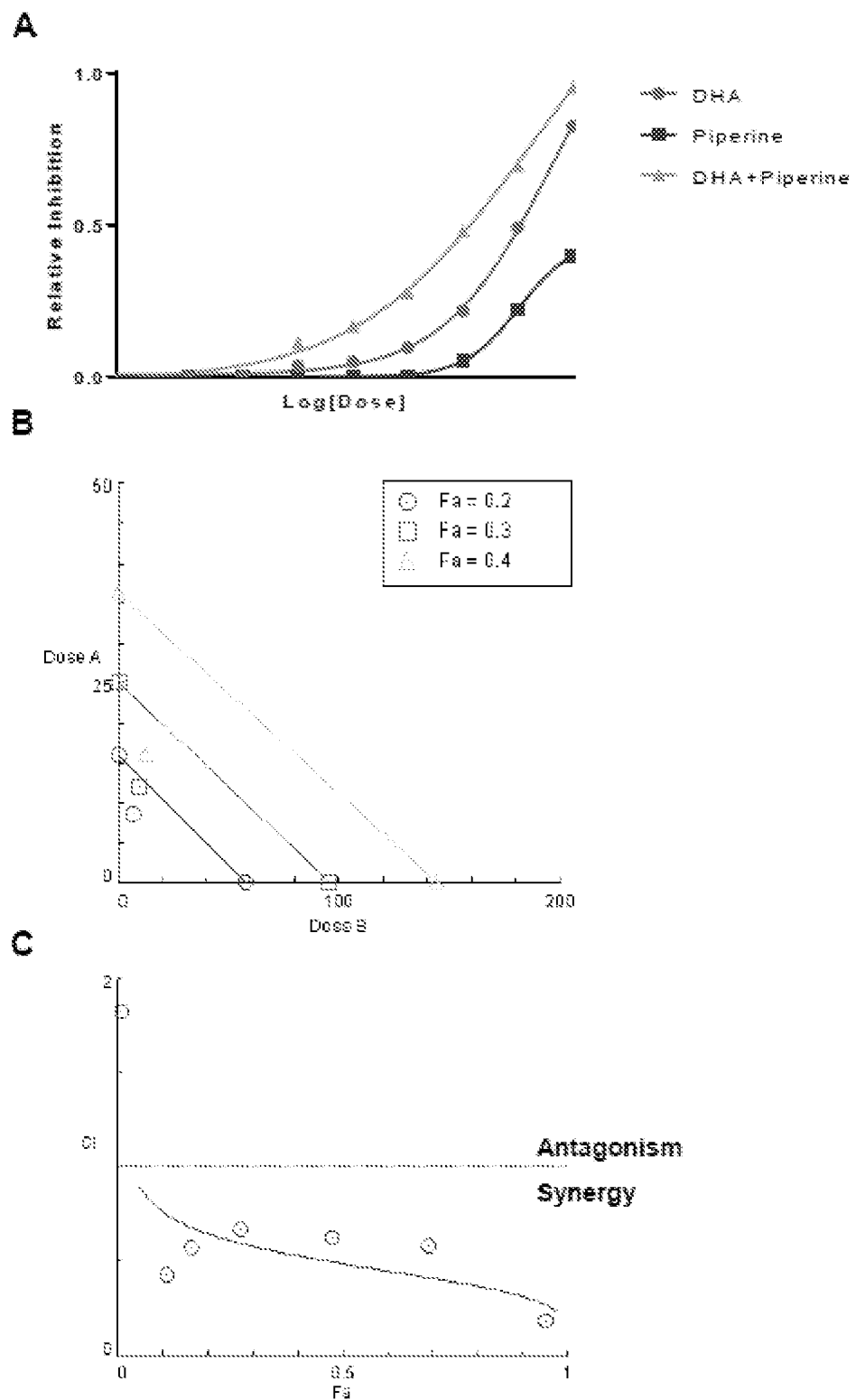
FIG. 18A is a series of dose-response curves of THP-1 cells treated with increasing doses of DHA, piperine, and DHA combined with piperine.
FIG. 18B is a series of isobolograms of THP-1 cells treated with DHA and piperine at low doses.
FIG. 18C is a CI plot of THP-1 cells treated with DHA and piperine across the entire dose range.

The effect of the combination of DHA and piperine on NLRP3 inflammasome activity was tested. The dose-response curves shown in FIG. 18A reveal that combining DHA with piperine produces a striking increase in efficacy compared to the single compounds.

The drug-drug interaction between DHA and piperine was formally assessed using CI analysis. As shown in the isobolograms in FIG. 18B, DHA and piperine are synergistic at low doses. The CI plot in FIG. 18C and CI values summarised in Table 4 confirm that DHA and piperine are strongly synergistic across all effective dose range.

Example 13

Combination of DHA and Plant Extracts

The combination of DHA and plant extracts was tested, focusing on low-dose ranges where the plant extracts remain in solution.

Figure 19:
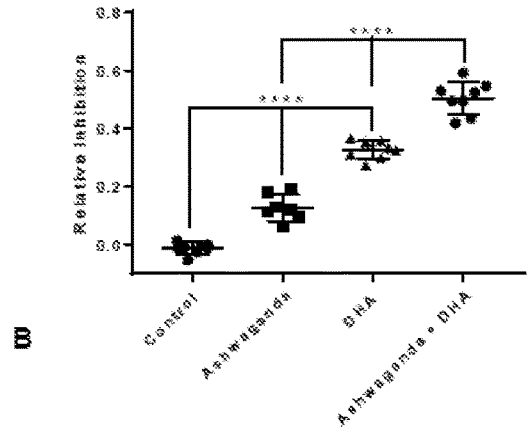
FIG. 19A is a graph showing the statistical comparison of the efficacy of empty vehicle (control), ashwagandha extract alone, DHA alone, and ashwagandha plant extract combined with DHA.
FIG. 19B is a comparison of the mean relative inhibition of the treatment groups of FIG. 19A.

First, the interaction between DHA and ashwaganda extract was investigated. From the data in FIG. 19A, DHA in combination with ashwagandha extract is significantly more efficacious than either DHA or ashwagandha extract alone. Importantly, comparison of the mean relative inhibition of the combined compounds revealed an inhibition level that is greater than additive compared to the single compounds (FIG. 19B). This finding is consistent with the observation that DHA and withaferin A are synergistic as observed above.

Figure 20:
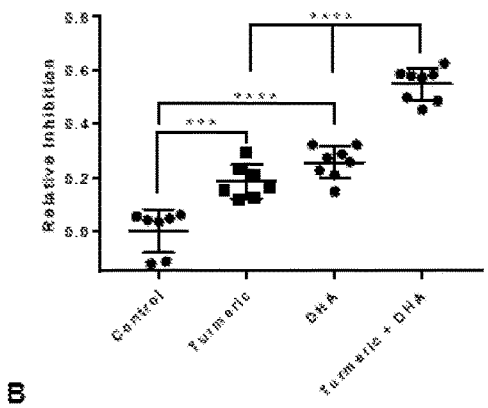
FIG. 20A is a graph showing the statistical comparison of the efficacy of empty vehicle (control), turmeric extract alone, DHA alone, and turmeric extract combined with DHA.
FIG. 20B is a comparison of the mean relative inhibition of the treatment groups of FIG. 20A.

Next, the combination of DHA and turmeric extract was investigated. The combination of DHA and turmeric extract is significantly more efficacious then DHA or turmeric extract alone, as can be see from the data in FIG. 20A. Comparison of the mean relative inhibition values of the single compounds versus the combination of DHA plus turmeric extract revealed that the combined compounds displayed an inhibitory effect that was greater than additive as predicted by the single compound inhibition values. This finding is consistent with the synergistic interaction between DHA and curcumin observed above.

Figure 21:
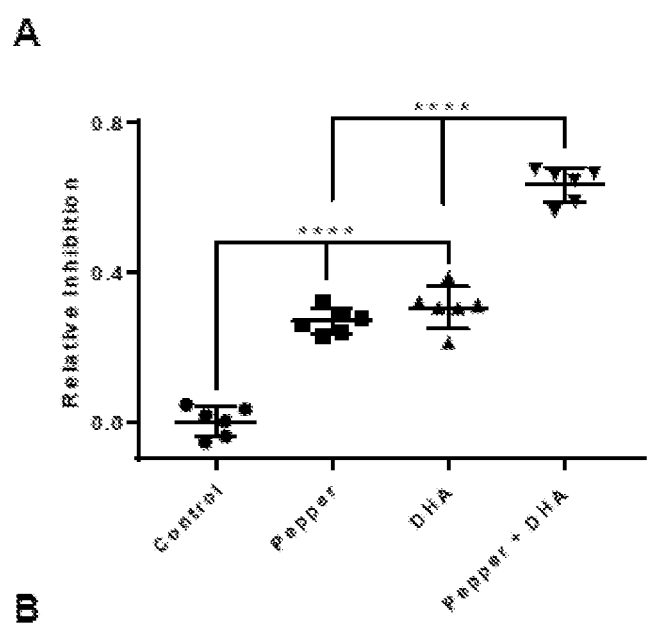
FIG. 21A is a graph showing the statistical comparison of the efficacy of empty vehicle (control), pepper extract alone, DHA alone, and pepper extract combined with DHA.
FIG. 21B is a comparison of the mean relative inhibition of the treatment groups of FIG. 21A.

Next, the interaction between DHA and pepper extract was investigated. The combination of DHA and pepper extract was significantly more efficacious than either compound alone (FIG. 21A), and comparison of the mean relative inhibition values revealed that the interaction between DHA and pepper extract was more than additive (FIG. 21B). This finding is consistent with the synergistic interaction between DHA and pure piperine observed above.

The interaction between DHA and a triple plant extract combination consisting of ashwagandha, turmeric and pepper plant extracts was tested. As shown above, the triple plant extract displays significant synergy and thus greatly improved efficacy compared to either single or double extract combinations. It was therefore important to determine whether addition of a fourth component, namely omega-3 fatty acids, could further improve efficacy above that observed for the synergistic extract combination.

Figure 22:
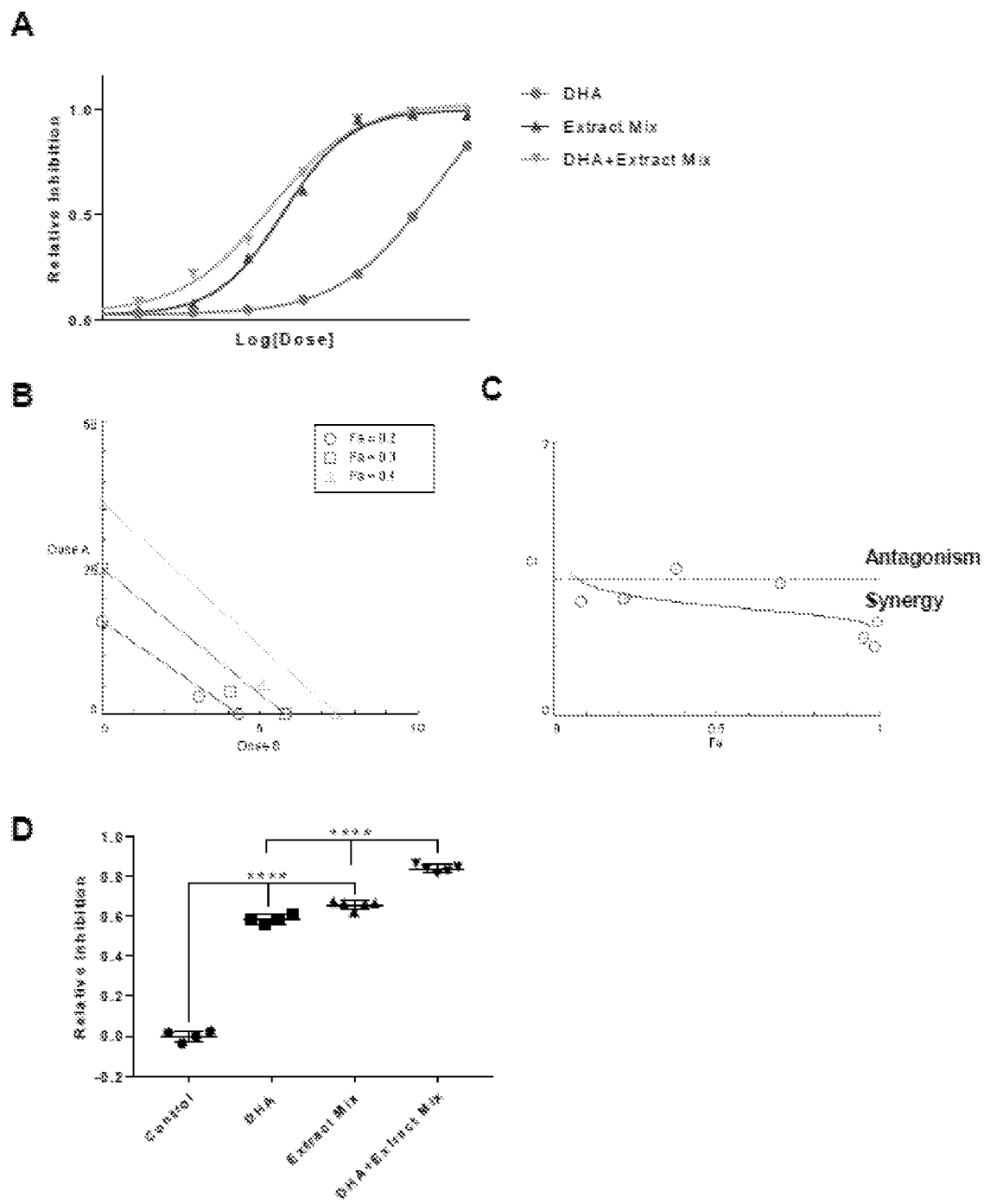
FIG. 22A is a series of dose-response curves of THP-1 cells treated with DHA alone, an extract mix (consisting of a combination of ashwagandha, turmeric and pepper extracts) alone, or DHA combined with the extract mix.
FIG. 22B is a series of isobolograms of THP-1 cells treated with plant extract mix plus DHA at low doses.
FIG. 22C is a CI plot of THP-1 cells treated with DHA plus the plant extract mix across all dose ranges.
FIG. 22D is a graph of the statistical comparison of THP-1 cells treated with empty vehicle (control), the plant extract mix alone, DHA alone, and the plant extract mix combined with DHA.

The dose-response curves for DHA, the triple extract mix, and DHA in combination with the triple plant extract mix, show that the addition of DHA to the triple extract mix did indeed improve efficacy when compared to the triple extract alone, especially within low dose ranges (FIG. 22A).

Unlike the single plant extracts, the triple plant extract combination displays a robust dose-response profile of a sufficient quality that permits the application of CI analyses. A synergy analysis of DHA in combination with the triple plant extract mix was undertaken. The CI analysis revealed that DHA synergises with the combined extracts within the low dose range of interest (FIG. 22B). The CI plot and values show that DHA and the plant extract mix synergise across the entire dose range (FIG. 22C and Table 4). Statistical analysis revealed that the combination of DHA with the plant extract mix significantly improved efficacy relative to the single treatments ($p<0.0001$).

As omega-3 fatty acids inhibit inflammation via the activation of autophagy (Shen et al., 2017; Williams-Bey et al., 2014), it is likely that synergy observed between DHA and the natural compounds and/or their cognate plant extracts is a common property for all dietary omega-3 fatty acids. To test this prediction, studies were undertaken to determine whether EPA behaved in a manner similar to DHA, and also to study the interaction between the triple plant extract combination of ashwagandha, turmeric and plant extracts and EPA. The dose-response curves for EPA, the triple extract mix, and EPA in combination with the triple plant extract mix, show that the addition of EPA to the triple extract mix did indeed improve efficacy when compared to the triple extract alone, which was especially evident within the low dose ranges (FIG. 23A).

Figure 23:
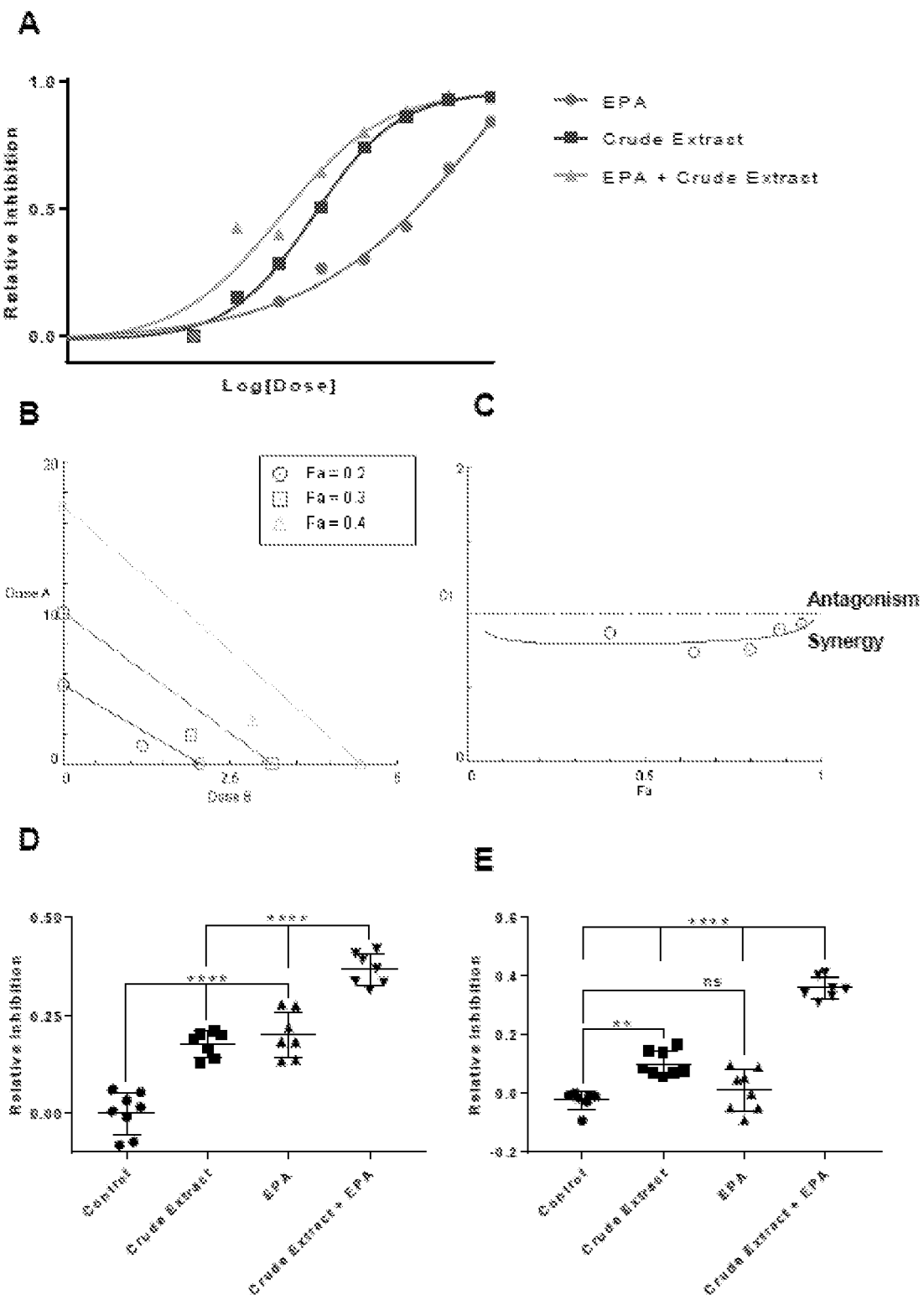
FIG. 23A is a series of dose-response curves of THP-1 cells treated with EPA alone, an extract mix (consisting of a combination of ashwagandha, turmeric and pepper extracts) alone, or EPA combined with the extract mix.
FIG. 23B is a series of isobolograms of THP-1 cells treated with plant extract mix plus EPA at low doses.
FIG. 23C is a CI plot of THP-1 cells treated with EPA plus the plant extract mix across all dose ranges.
FIG. 23D is a graph of the statistical comparison of THP-1 cells treated with empty vehicle (control), the plant extract mix alone, EPA alone, and the plant extract mix combined with EPA.
FIG. 23E is a graph of the statistical comparison of THP-1 cells treated with empty vehicle (control), the plant extract mix alone, EPA alone, and the plant extract mix combined with EPA.

A synergy analysis of EPA in combination with the triple plant extract mix revealed that EPA synergises with the combined extracts within the low dose range of interest (FIG. 23B). The CI plot and values show that EPA and the plant extract mix synergise across the entire dose range (FIG. 23C and Table 4). Statistical analysis revealed that the combination of EPA with the plant extract mix significantly improved efficacy relative to the single extracts ($p<0.0001$) (FIG. 23D). From FIG. 23E, it can be seen that the dose of EPA alone did not cause significant inhibition of inflammation. However, strikingly, at low doses where EPA alone had no significant effect, EPA was found to potential the efficacy of the plant extract mix approximately three-fold ($p<0.0001$) (FIG. 23E).

Thus, the omega-3 fatty acid DHA synergises with the natural compounds withaferin A, curcumin and piperine. In addition, the combination of DHA with the cognate plant extracts (namely ashwagandha, turmeric and pepper) is more than additive. Finally, the omega-3 fatty acids DHA and EPA are both synergistic with the triple plant extract (ashwagandha plus turmeric plus pepper).

As omega-3 fatty acids are known to inhibit inflammation via the activation of autophagy (Shen et al., 2017; Williams-Bey et al., 2014), and because the two structurally diverse omega-3 fatty acids, DHA and EPA, both behave synergistically when combined with natural plant extracts, the synergy observed between DHA or EPA and the natural compounds and/or their cognate plant extracts is likely a synergy that operates across all dietary omega-3 fatty acids.

Collectively these data show that omega-3 fatty acids increase the efficacy of both single and combined natural products and plant extracts in a manner that is more than additive.

TABLE 4

Summary of CI values for DHA in combination with natural compounds and their cognate ashwagandha, turmeric and pepper extracts in combination.

| | CI Value | | | | |
|---|---|---|---|---|---|
| Fa | withaferin A + DHA | curcumin + DHA | piperine + DHA | extract mix + DHA | extract mix + EPA |
| 0.05 | 0.84865 | 1.04397 | 0.89192 | 1.04785 | 0.88552 |
| 0.1 | 0.82530 | 0.94986 | 0.76470 | 0.96904 | 0.83854 |
| 0.15 | 0.81690 | 0.90659 | 0.69549 | 0.92729 | 0.81988 |
| 0.2 | 0.81331 | 0.88045 | 0.64768 | 0.89888 | 0.81038 |
| 0.25 | 0.81200 | 0.86258 | 0.61076 | 0.87717 | 0.80521 |
| 0.3 | 0.81200 | 0.84950 | 0.58029 | 0.85938 | 0.80254 |
| 0.35 | 0.81289 | 0.83951 | 0.55397 | 0.84412 | 0.80150 |
| 0.4 | 0.81445 | 0.83169 | 0.53046 | 0.83054 | 0.80166 |
| 0.45 | 0.81659 | 0.82549 | 0.50889 | 0.81814 | 0.80280 |
| 0.5 | 0.81926 | 0.82058 | 0.48862 | 0.80652 | 0.80480 |
| 0.55 | 0.82250 | 0.81676 | 0.46919 | 0.79541 | 0.80764 |
| 0.6 | 0.82636 | 0.81392 | 0.45018 | 0.78455 | 0.81137 |
| 0.65 | 0.83097 | 0.81205 | 0.43119 | 0.77373 | 0.81611 |
| 0.7 | 0.83653 | 0.81120 | 0.41181 | 0.76269 | 0.82211 |
| 0.75 | 0.84338 | 0.81155 | 0.39151 | 0.75111 | 0.82976 |
| 0.8 | 0.85213 | 0.81353 | 0.36953 | 0.73855 | 0.83981 |
| 0.85 | 0.86397 | 0.81800 | 0.34461 | 0.72426 | 0.85374 |
| 0.9 | 0.88170 | 0.82715 | 0.31416 | 0.70667 | 0.87505 |
| 0.95 | 0.91493 | 0.84887 | 0.27068 | 0.68112 | 0.91577 |
| 0.97 | 0.94182 | 0.86896 | 0.24355 | 0.66477 | 0.94918 |

It can therefore be seen that the invention advantageously provides a combination of natural products that can be used to treat disease states involving sterile inflammation. Particular combinations of natural products have been surprisingly found to have a synergistic effect when combined at low doses. Advantageously, the use of synergistic natural product combinations at low doses has therapeutic advantages, including (i) an increased therapeutic efficacy, thus providing better disease management; (ii) the ability to apply a reduced dosage scheme whilst maintaining efficacy, thereby minimising side-effects and toxicity during long-term treatment of chronic diseases; and (iii) effective use of natural compounds that have poor bioavailability.

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

CITATION LIST

British Pharmacopoeia (BP)

Chanput, W., Mes, J. J., and Wichers, H. J. (2014). THP-1 cell line: an in vitro cell model for immune modulation approach. Int Immunopharmacol 23, 37-45.

Chen, G. Y., and Nunez, G. (2010). Sterile inflammation: sensing and reacting to damage. Nat Rev Immunol 10, 826-837.

Chou, T. C. (2002). Synergy determination issues. J Virol 76, 10577; author reply 10578.

Chou, T. C. (2006). Theoretical basis, experimental design, and computerized simulation of synergism and antagonism in drug combination studies. Pharmacol Rev 58, 621-681.

Chou, T. C. (2008). Preclinical versus clinical drug combination studies. Leuk Lymphoma 49, 2059-2080.

Chou, T. C. (2010). Drug combination studies and their synergy quantification using the Chou-Talalay method. Cancer Res 70, 440-446.

Chou, T. C., and Talalay, P. (1981). Generalized equations for the analysis of inhibitions of Michaelis-Menten and higher-order kinetic systems with two or more mutually exclusive and nonexclusive inhibitors. Eur J Biochem 115, 207-216.

Chou, T. C., and Talalay, P. (1984). Quantitative analysis of dose-effect relationships: the combined effects of multiple drugs or enzyme inhibitors. Adv Enzyme Regul 22, 27-55.

Chou, T. C. M., N. (2005). CompuSyn for Drug Combinations: PC Software and User's Guide: A Computer Program for Quantitation of Synergism and Antagonism in Drug Combinations, and the Determination of IC50 and ED50 and LD50 Values. ComboSyn Inc, Paramus, (N.J.).

Chow, M. T., Sceneay, J., Paget, C., Wong, C. S., Duret, H., Tschopp, J., Moller, A., and Smyth, M. J. (2012). NLRP3 suppresses NK cell-mediated responses to carcinogen-induced tumors and metastases. Cancer Res 72, 5721-5732.

Coll, R. C., Robertson, A. A., Chae, J. J., Higgins, S. C., Munoz-Planillo, R., Inserra, M. C., Vetter, I., Dungan, L. S., Monks, B. G., Stutz, A., et al. (2015). A small-molecule inhibitor of the NLRP3 inflammasome for the treatment of inflammatory diseases. Nat Med 21, 248-255.

Conway, R., and McCarthy, G. M. (2018). Calcium-Containing Crystals and Osteoarthritis: an Unhealthy Alliance. Curr Rheumatol Rep 20, 13.

Debye, B., Schmulling, L., Zhou, L., Rune, G., Beyer, C., and Johann, S. (2018). Neurodegeneration and NLRP3 inflammasome expression in the anterior thalamus of SOD1(G93A) ALS mice. Brain Pathol 28, 14-27.

Deguchi, A. (2015). Curcumin targets in inflammation and cancer. Endocr Metab Immune Disord Drug Targets 15, 88-96.

Delazar, A., Nahar, L., Hamedeyazdan, S., and Sarker, S. D. (2012). Microwave-assisted extraction in natural products isolation. Methods Mol Biol 864, 89-115.

Dinarello, C. A. (2011). A clinical perspective of IL-1beta as the gatekeeper of inflammation. Eur J Immunol 41, 1203-1217.

Dubey, S., Yoon, H., Cohen, M. S., Nagarkatti, P., Nagarkatti, M., and Karan, D. (2018). Withaferin A Associated Differential Regulation of Inflammatory Cytokines. Front Immunol 9, 195.

Dunster, J. L. (2016). The macrophage and its role in inflammation and tissue repair: mathematical and systems biology approaches. Wiley Interdiscip Rev Syst Biol Med 8, 87-99.

Esser, N., Legrand-Poels, S., Piette, J., Scheen, A. J., and Paquot, N. (2014). Inflammation as a link between obesity, metabolic syndrome and type 2 diabetes. Diabetes Res Clin Pract 105, 141-150.

Ferrucci, L., and Fabbri, E. (2018). Inflammageing: chronic inflammation in ageing, cardiovascular disease, and frailty. Nat Rev Cardiol 15, 505-522.

Fleshner, M., Frank, M., and Maier, S. F. (2017). Danger Signals and Inflammasomes: Stress-Evoked Sterile Inflammation in Mood Disorders. Neuropsychopharmacology 42, 36-45.

Fritsche, K. (2006). Fatty acids as modulators of the immune response. Annu Rev Nutr 26, 45-73.

Fuchs, T., Kelly, J. A., Simon, E., Sivils, K. L., and Hermel, E. (2016). The anti-inflammatory CASPASE-12 gene does not influence SLE phenotype in African-Americans. Immunol Lett 173, 21-25.

Gao, J., Liu, R. T., Cao, S., Cui, J. Z., Wang, A., To, E., and Matsubara, J. A. (2015). NLRP3 inflammasome: activation and regulation in age-related macular degeneration. Mediators Inflamm 2015, 690243.

Geeraerts, X., Bolli, E., Fendt, S. M., and Van Ginderachter, J. A. (2017). Macrophage Metabolism As Therapeutic Target for Cancer, Atherosclerosis, and Obesity. Front Immunol 8, 289.

Ghosh, S., Banerjee, S., and Sil, P. C. (2015). The beneficial role of curcumin on inflammation, diabetes and neurodegenerative disease: A recent update. Food Chem Toxicol 83, 111-124.

Goldberg, E. L., and Dixit, V. D. (2015). Drivers of age-related inflammation and strategies for healthspan extension. Immunol Rev 265, 63-74.

Guarda, G., Zenger, M., Yazdi, A. S., Schroder, K., Ferrero, I., Menu, P., Tardivel, A., Mattmann, C., and Tschopp, J. (2011). Differential expression of NLRP3 among hematopoietic cells. J Immunol 186, 2529-2534.

Guo, H., Callaway, J. B., and Ting, J. P. (2015). Inflammasomes: mechanism of action, role in disease, and therapeutics. Nat Med 21, 677-687.

Guo, W., Sun, Y., Liu, W., Wu, X., Guo, L., Cai, P., Wu, X., Wu, X., Shen, Y., Shu, Y., et al. (2014). Small molecule-driven mitophagy-mediated NLRP3 inflammasome inhibition is responsible for the prevention of colitis-associated cancer. Autophagy 10, 972-985.

Guo, Z., Yu, S., Chen, X., Ye, R., Zhu, W., and Liu, X. (2016). NLRP3 Is Involved in Ischemia/Reperfusion Injury. CNS Neurol Disord Drug Targets 15, 699-712.

Haneklaus, M., and O'Neill, L. A. (2015). NLRP3 at the interface of metabolism and inflammation. Immunol Rev 265, 53-62.

Heneka, M. T., Kummer, M. P., Stutz, A., Delekate, A., Schwartz, S., Vieira-Saecker, A., Griep, A., Axt, D., Remus, A., Tzeng, T. C., et al. (2013). NLRP3 is activated in Alzheimer's disease and contributes to pathology in APP/PS1 mice. Nature 493, 674-678.

Herman, F. J., and Pasinetti, G. M. (2018). Principles of inflammasome priming and inhibition: Implications for psychiatric disorders. Brain Behav Immun.

Ireland, D. J., Nathan, E. A., Li, S., Charles, A. K., Stinson, L. F., Kemp, M. W., Newnham, J .P., and Keelan, J. A. (2017). Preclinical evaluation of drugs to block inflammation-driven preterm birth. Innate Immun 23, 20-33.

Kapetanovic, R., Bokil, N. J., and Sweet, M. J. (2015). Innate immune perturbations, accumulating DAMPs and inflammasome dysregulation: A ticking time bomb in ageing. Ageing Res Rev 24, 40-53.

Kaufmann, F. N., Costa, A. P., Ghisleni, G., Diaz, A. P., Rodrigues, A. L. S., Peluffo, H., and Kaster, M. P. (2017). NLRP3 inflammasome-driven pathways in depression: Clinical and preclinical findings. Brain Behav Immun 64, 367-383.

Koelwyn, G. J., Corr, E. M., Erbay, E., and Moore, K. J. (2018). Regulation of macrophage immunometabolism in atherosclerosis. Nat Immunol 19, 526-537.

Lee, E., Hwang, I., Park, S., Hong, S., Hwang, B., Cho, Y., Son, J., and Yu, J. W. (2018). MPTP-driven NLRP3 inflammasome activation in microglia plays a central role in dopaminergic neurodegeneration. Cell Death Differ.

Lee, I. C., and Choi, B. Y. (2016). Withaferin-A-A Natural Anticancer Agent with Pleitropic Mechanisms of Action. Int J Mol Sci 17, 290.

Leemans, J. C., Cassel, S. L., and Sutterwala, F. S. (2011). Sensing damage by the NLRP3 inflammasome. Immunol Rev 243, 152-162.

Liao, P. C., Chao, L. K., Chou, J. C., Dong, W. C., Lin, C. N., Lin, C. Y., Chen, A., Ka, S. M., Ho, C. L., and Hua, K. F. (2013). Lipopolysaccharide/adenosine triphosphate-mediated signal transduction in the regulation of NLRP3 protein expression and caspase-1-mediated interleukin-1beta secretion. Inflamm Res 62, 89-96.

Lopez-Castejon, G., and Brough, D. (2011). Understanding the mechanism of IL-1beta secretion. Cytokine Growth Factor Rev 22, 189-195.

Mangan, M. S. J., Olhava, E. J., Roush, W. R., Seidel, H. M., Glick, G. D., and Latz, E. (2018). Targeting the NLRP3 inflammasome in inflammatory diseases. Nat Rev Drug Discov 17, 588-606.

Marchetti, C., Swartzwelter, B., Koenders, M. I., Azam, T., Tengesdal, I. W., Powers, N., de Graaf, D. M., Dinarello, C. A., and Joosten, L. A. B. (2018). NLRP3 inflammasome inhibitor OLT1177 suppresses joint inflammation in murine models of acute arthritis. Arthritis Res Ther 20, 169.

Marneros, A. G. (2013). NLRP3 inflammasome blockade inhibits VEGF-A-induced age-related macular degeneration. Cell Rep 4, 945-958.

'Martindale: The complete drug reference.' London: Pharmaceutical Press, $37^{th}$ Ed., Sweetman S (Ed.), (2011)

Martirosyan, A., Petrek, M., Navratilova, Z., Blbulyan, A., Boyajyan, A., and Manukyan, G. (2015). Differential regulation of proinflammatory mediators following LPS- and ATP-induced activation of monocytes from patients with antiphospholipid syndrome. Biomed Res Int 2015, 292851.

Mathews, R. J., Robinson, J. I., Battellino, M., Wong, C., Taylor, J. C., Biologics in Rheumatoid Arthritis, G., Genomics Study, S., Eyre, S., Churchman, S. M., Wilson, A. G., et al. (2014). Evidence of NLRP3-inflammasome activation in rheumatoid arthritis (RA); genetic variants within the NLRP3-inflammasome complex in relation to susceptibility to RA and response to anti-TNF treatment. Ann Rheum Dis 73, 1202-1210.

McAllister, M. J., Chemaly, M., Eakin, A. J., Gibson, D. S., and McGilligan, V. E. (2018). NLRP3 as a potentially novel biomarker for the management of osteoarthritis. Osteoarthritis Cartilage 26, 612-619.

McBride, M. J., Foley, K. P., D'Souza, D. M., Li, Y. E., Lau, T. C., Hawke, T. J., and Schertzer, J. D. (2017). The NLRP3 inflammasome contributes to sarcopenia and lower muscle glycolytic potential in old mice. Am J Physiol Endocrinol Metab 313, E222-E232.

McKenna, M. K., Gachuki, B. W., Alhakeem, S. S., Oben, K. N., Rangnekar, V. M., Gupta, R. C., and Bondada, S. (2015). Anti-cancer activity of withaferin A in B-cell lymphoma. Cancer Biol Ther 16, 1088-1098.

Mezzasoma, L., Antognelli, C., and Talesa, V. N. (2016). Atrial natriuretic peptide down-regulates LPS/ATP-mediated IL-1beta release by inhibiting NF-kB, NLRP3 inflammasome and caspase-1 activation in THP-1 cells. Immunol Res 64, 303-312.

Minutoli, L., Puzzolo, D., Rinaldi, M., Irrera, N., Marini, H., Arcoraci, V., Bitto, A., Crea, G., Pisani, A., Squadrito, F., et al. (2016). ROS-Mediated NLRP3 Inflammasome Activation in Brain, Heart, Kidney, and Testis Ischemia/Reperfusion Injury. Oxid Med Cell Longev 2016, 2183026.

Mortimer, L., Moreau, F., MacDonald, J. A., and Chadee, K. (2016). NLRP3 inflammasome inhibition is disrupted in a group of auto-inflammatory disease CAPS mutations. Nat Immunol 17, 1176-1186.

Naji, A., Muzembo, B. A., Yagyu, K., Baba, N., Deschaseaux, F., Sensebe, L., and Suganuma, N. (2016). Endocytosis of indium-tin-oxide nanoparticles by macrophages provokes pyroptosis requiring NLRP3-ASC-Caspase1 axis that can be prevented by mesenchymal stem cells. Sci Rep 6, 26162.

Nakahira, K., Hisata, S., and Choi, A. M. (2015). The Roles of Mitochondrial Damage-Associated Molecular Patterns in Diseases. Antioxid Redox Signal 23, 1329-1350.

Nakayama, M. (2018). Macrophage Recognition of Crystals and Nanoparticles. Front Immunol 9, 103.

Niemiec, M. J., Grumaz, C., Ermert, D., Desel, C., Shankar, M., Lopes, J. P., Mills, I. G., Stevens, P., Sohn, K., and Urban, C. F. (2017). Dual transcriptome of the immediate neutrophil and Candida albicans interplay. BMC Genomics 18, 696.

Pavillard, L. E., Marin-Aguilar, F., Bullon, P., and Cordero, M. D. (2018). Cardiovascular diseases, NLRP3 inflammasome, and western dietary patterns. Pharmacol Res 131, 44-50.

Peiseler, M., and Kubes, P. (2018). Macrophages play an essential role in trauma-induced sterile inflammation and tissue repair. Eur J Trauma Emerg Surg 44, 335-349.

Pennisi, M., Crupi, R., Di Paola, R., Ontario, M. L., Bella, R., Calabrese, E. J., Crea, R., Cuzzocrea, S., and Calabrese, V. (2017). Inflammasomes, hormesis, and antioxidants in neuroinflammation: Role of NRLP3 in Alzheimer disease. J Neurosci Res 95, 1360-1372.

Rowe R C, Sheskey P J, Quinn ME (Ed.), 'Handbook of Pharmaceutical Excipients', 6$^{th}$ Ed., London: Pharmaceutical Press (2009)

Rubartelli, A. (2014). DAMP-Mediated Activation of NLRP3-Inflammasome in Brain Sterile Inflammation: The Fine Line between Healing and Neurodegeneration. Front Immunol 5, 99.

Sevenich, L. (2018). Brain-Resident Microglia and Blood-Borne Macrophages Orchestrate Central Nervous System Inflammation in Neurodegenerative Disorders and Brain Cancer. Front Immunol 9, 697.

Shen, L., Yang, Y., Ou, T., Key, C. C., Tong, S. H., Sequeira, R. C., Nelson, J. M., Nie, Y., Wang, Z., Boudyguina, E., et al. (2017). Dietary PUFAs attenuate NLRP3 inflammasome activation via enhancing macrophage autophagy. J Lipid Res 58, 1808-1821.

Snouwaert, J. N., Nguyen, M., Repenning, P. W., Dye, R., Livingston, E. W., Kovarova, M., Moy, S. S., Brigman, B. E., Bateman, T. A., Ting, J. P., et al. (2016). An NLRP3 Mutation Causes Arthropathy and Osteoporosis in Humanized Mice. Cell Rep 17, 3077-3088.

So, A. K., and Martinon, F. (2017). Inflammation in gout: mechanisms and therapeutic targets. Nat Rev Rheumatol 13, 639-647.

Tabas, I., and Bornfeldt, K. E. (2016). Macrophage Phenotype and Function in Different Stages of Atherosclerosis. Circ Res 118, 653-667.

United States Pharmacopeia and National Formulary (USP-NF)

Vande Walle, L., Van Opdenbosch, N., Jacques, P., Fossoul, A., Verheugen, E., Vogel, P., Beyaert, R., Elewaut, D., Kanneganti, T. D., van Loo, G., et al. (2014). Negative regulation of the NLRP3 inflammasome by A20 protects against arthritis. Nature 512, 69-73.

Wang, L., Chen, K., Wan, X., Wang, F., Guo, Z., and Mo, Z. (2017). NLRP3 inflammasome activation in mesenchymal stem cells inhibits osteogenic differentiation and enhances adipogenic differentiation. Biochem Biophys Res Commun 484, 871-877.

Williams-Bey, Y., Boularan, C., Vural, A., Huang, N. N., Hwang, I. Y., Shan-Shi, C., and Kehrl, J. H. (2014). Omega-3 free fatty acids suppress macrophage inflammasome activation by inhibiting NF-kappaB activation and enhancing autophagy. PLoS One 9, e97957.

Xiao, Y., Xu, W., and Su, W. (2018). NLRP3 inflammasome: A likely target for the treatment of allergic diseases. Clin Exp Allergy.

Xie, Q., Shen, W. W., Zhong, J., Huang, C., Zhang, L., and Li, J. (2014). Lipopolysaccharide/adenosine triphosphate induces IL1beta and IL-18 secretion through the NLRP3 inflammasome in RAW264.7 murine macrophage cells. Int J Mol Med 34, 341-349.

Xu, L., Zhang, L., Wang, Z., Li, C., Li, S., Li, L., Fan, Q., and Zheng, L. (2018). Melatonin Suppresses Estrogen Deficiency-Induced Osteoporosis and Promotes Osteoblastogenesis by Inactivating the NLRP3 Inflammasome. Calcif Tissue Int.

Yan, Y., Jiang, W., Spinetti, T., Tardivel, A., Castillo, R., Bourquin, C., Guarda, G., Tian, Z., Tschopp, J., and Zhou, R. (2013). Omega-3 fatty acids prevent inflammation and metabolic disorder through inhibition of NLRP3 inflammasome activation. Immunity 38, 1154-1163.

Ying, X., Yu, K., Chen, X., Chen, H., Hong, J., Cheng, S., and Peng, L. (2013). Piperine inhibits LPS induced expression of inflammatory mediators in RAW 264.7 cells. Cell Immunol 285, 49-54.

Zhang, B., Xu, D., She, L., Wang, Z., Yang, N., Sun, R., Zhang, Y., Yan, C., Wei, Q., Aa, J., et al. (2018). Silybin inhibits NLRP3 inflammasome assembly through the NAD(+)/SIRT2 pathway in mice with nonalcoholic fatty liver disease. FASEB J 32, 757-767.

Zhang, J., Fu, S., Sun, S., Li, Z., and Guo, B. (2014). Inflammasome activation has an important role in the development of spontaneous colitis. Mucosal Immunol 7, 1139-1150.

Zhang, M. J., and Spite, M. (2012). Resolvins: anti-inflammatory and proresolving mediators derived from omega-3 polyunsaturated fatty acids. Annu Rev Nutr 32, 203-227.

Zhong, Z., Sanchez-Lopez, E., and Karin, M. (2016). Autophagy, NLRP3 inflammasome and auto-inflammatory/immune diseases. Clin Exp Rheumatol 34, 12-16.

Zhou, K., Shi, L., Wang, Y., Chen, S., and Zhang, J. (2016). Recent Advances of the NLRP3 Inflammasome in Central Nervous System Disorders. J Immunol Res 2016, 9238290.

The invention claimed is:

1. A composition comprising one or more natural products selected from the group consisting of compounds that can be isolated from plants of the genera *Withania* present within the concentration range of 3-350 nM; one or more omega-3 fatty acids present within the concentration range of 1340 nM 85 µM, and:
   (i) an extract of turmeric present within the concentration range of 99 nM 21 µM; or
   (ii) an extract of pepper present within the concentration range of 135 nM-410 µM; or
   (iii) an extract of turmeric present within the concentration range of 99 nM-21 µM, and an extract of pepper present within the concentration range of 135 nM-410 µM;

wherein the combination of one or more omega-3 fatty acids, and extracts from *Withania*, turmeric and/or pepper is a synergistic combination, wherein the synergistic combination is within a low dose range of up to Fa 0.65.

2. The composition of claim 1, wherein the one or more natural products selected from the group consisting of compounds that can be isolated from plants of the genera *Withania*, comprises an extract of ashwagandha.

3. The composition of claim 1, wherein the one or more natural products selected from the group consisting of compounds that can be isolated from plants of the genera *Withania*, comprises withaferin A.

4. The composition of claim 1, wherein the one or more omega-3 fatty acids are selected from the group consisting of docosahexaenoic acid (DHA) and eicosapentaenoic acid (EPA).

5. The composition of claim 4, wherein the composition comprises docosahexaenoic acid (DHA) and eicosapentaenoic acid (EPA).

6. The composition of claim 4, wherein the composition comprises DHA.

7. The composition of claim 4, wherein the composition comprises EPA.

8. The composition of claim 1, further comprising one or more pharmaceutically acceptable carriers, diluents and/or excipients.

9. The composition of claim 1, wherein the composition is formulated for oral administration.

10. The composition of claim 1, wherein the composition is in the form of a powder, a liquid solution, a liposomal solution, a suspension, a dispersion, an emulsion, a tablet, a pill or a capsule.

11. A method of protecting a subject from sterile inflammation, the method comprising administering to the subject a therapeutically effective amount of a composition of claim 1.

12. A method of treating and/or preventing a condition associated with sterile inflammation, the method comprising administering to the subject a therapeutically effective amount of a composition of claim 1.

* * * * *